(12) United States Patent
Berry

(10) Patent No.: US 11,793,651 B2
(45) Date of Patent: Oct. 24, 2023

(54) EXPANDABLE IMPLANT

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 0 days.

(21) Appl. No.: 17/140,761

(22) Filed: Jan. 4, 2021

(65) Prior Publication Data

US 2022/0211512 A1  Jul. 7, 2022

(51) Int. Cl.
  *A61F 2/44* (2006.01)
  *A61F 2/30* (2006.01)

(52) U.S. Cl.
  CPC .... *A61F 2/442* (2013.01); *A61F 2002/30153* (2013.01); *A61F 2002/30537* (2013.01)

(58) Field of Classification Search
  CPC ...... A61F 2/4455; A61F 2/446; A61F 2/4465; A61F 2/447; A61F 2002/30579
  See application file for complete search history.

(56) References Cited

U.S. PATENT DOCUMENTS

| | | | |
|---|---|---|---|
| 8,940,049 B1 | 1/2015 | Jimenez et al. | |
| 10,363,142 B2 | 7/2019 | McClintock | |
| 2007/0239160 A1* | 10/2007 | Zipnick | A61B 17/3421 606/86 A |
| 2010/0076493 A1* | 3/2010 | Fauth | A61F 2/4684 606/279 |
| 2012/0004729 A1* | 1/2012 | Zipnick | A61B 17/7062 623/17.16 |
| 2014/0128977 A1* | 5/2014 | Glerum | A61F 2/447 623/17.16 |
| 2014/0343677 A1 | 11/2014 | Davis et al. | |
| 2016/0120660 A1* | 5/2016 | Melkent | A61F 2/447 623/17.16 |
| 2017/0128226 A1* | 5/2017 | Faulhaber | A61F 2/30767 |
| 2020/0268524 A1* | 8/2020 | Glerum | A61F 2/4425 |
| 2020/0281741 A1* | 9/2020 | Grotz | A61F 2/447 |

FOREIGN PATENT DOCUMENTS

| | | | |
|---|---|---|---|
| WO | 2015063721 A1 | 5/2015 | |
| WO | 2015198335 A1 | 12/2015 | |
| WO | WO-2015198335 A1 * | 12/2015 | ............ A61F 2/4611 |

OTHER PUBLICATIONS

Extended European Search Report for European Patent Application No. 21218437.8, dated Jun. 10, 2022.

\* cited by examiner

*Primary Examiner* — Eduardo C Robert
*Assistant Examiner* — Michelle C Eckman
(74) *Attorney, Agent, or Firm* — McCarter & English, LLP; James M. Smedley; Alex Korona

(57) ABSTRACT

An implant is disclosed. The implant has a first endplate, a second endplate, a base disposed between the first endplate and the second endplate, a plurality of adjustment arms operably connecting the base with the first endplate and the second endplate, and a plurality of pins disposed on at least one of the first endplate and the second endplate. The plurality of pins have different lengths. The plurality of adjustment arms are rotatably connected to a plurality of hubs that are axially slidable on at least some of the plurality of pins.

17 Claims, 18 Drawing Sheets

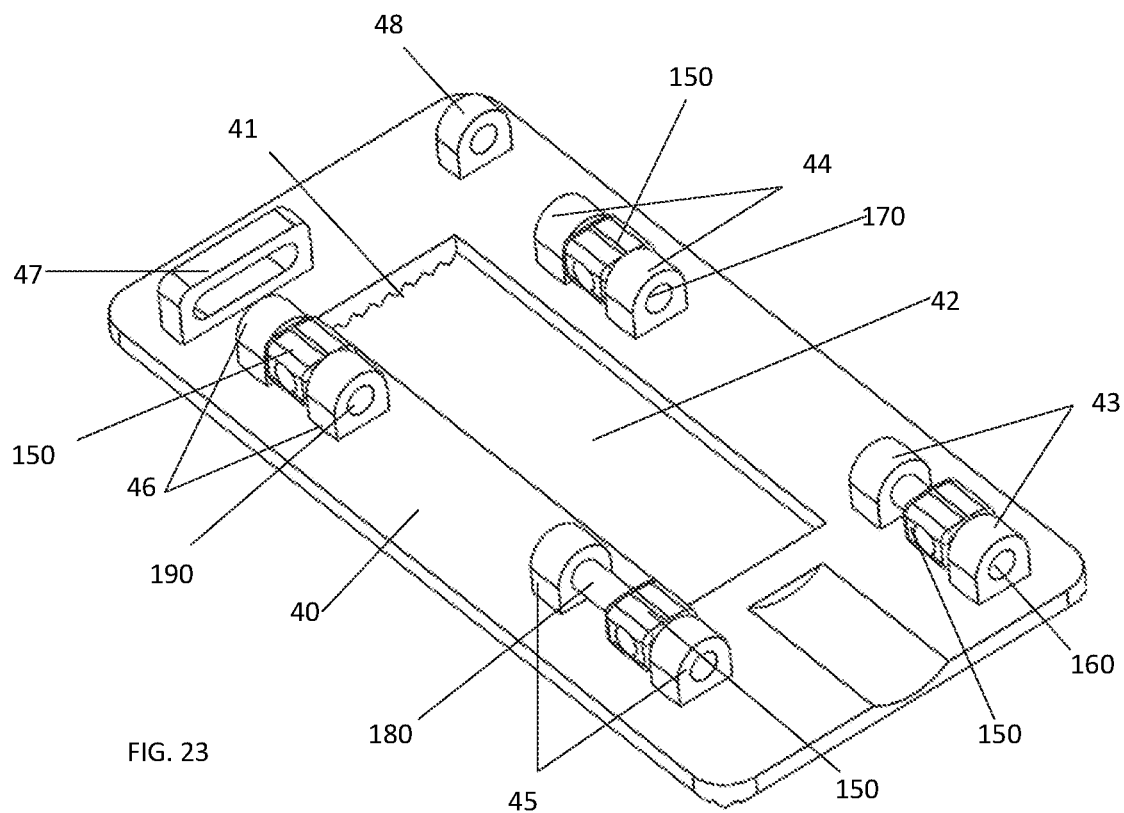
FIG. 23
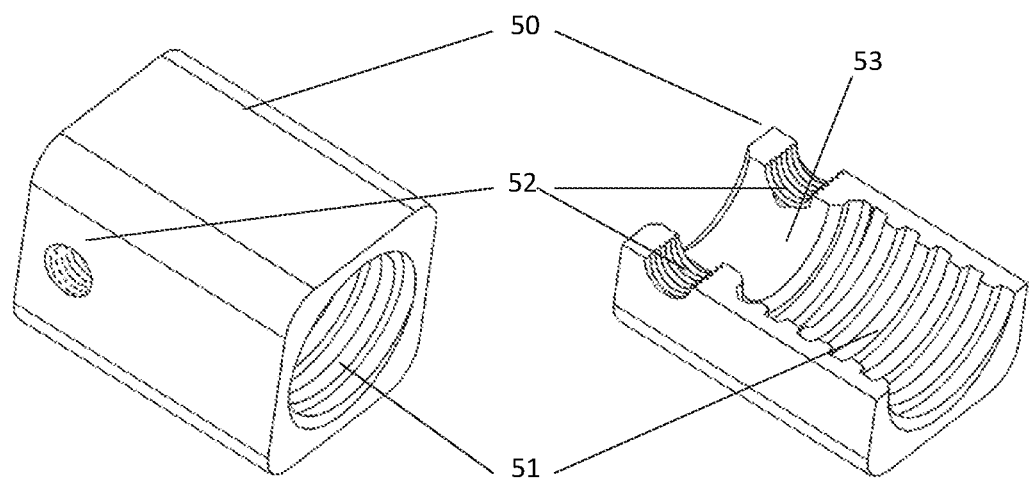
FIG. 24
FIG. 25

EXPANDABLE IMPLANT

TECHNICAL FIELD

The present disclosure is directed to an implant, and more particularly, to an expandable implant.

BACKGROUND OF THE DISCLOSURE

Conventional spinal implants are used to treat conditions, injuries, and diseases that degrade a functioning of the spinal column. Existing spinal implants may be adjustable to assist in treating such conditions in the spinal column.

Conventional implants, however, are often moved or displaced from their appropriate positions prior to achieving desired growth or fusion with spinal bone structure. Further, conventional implants do not provide a sufficient degree of adjustability for achieving a desired position relative to the spinal column. For example, conventional implants do not provide sufficient adjustability in desired directions, and do not provide sufficient adjustment between desired directions independently from each other in order to achieve and maintain a desired position relative to the spinal column.

The exemplary disclosed system and method of the present disclosure is directed to overcoming one or more of the shortcomings set forth above and/or other deficiencies in existing technology.

SUMMARY OF THE DISCLOSURE

In one exemplary aspect, the present disclosure is directed to an implant. The implant includes a first endplate, a second endplate, a base disposed between the first endplate and the second endplate, a plurality of adjustment arms operably connecting the base with the first endplate and the second endplate, and a plurality of pins disposed on at least one of the first endplate and the second endplate. The plurality of pins have different lengths. The plurality of adjustment arms are rotatably connected to a plurality of hubs that are axially slidable on at least some of the plurality of pins.

In another aspect, the present disclosure is directed to an implant. The implant includes a first endplate, a second endplate, a base disposed between the first endplate and the second endplate, a plurality of adjustment arms, which include a plurality of height adjustment arms and a plurality of lordotic adjustment arms, operably connecting the base with the first endplate and the second endplate, a plurality of pins disposed on at least one of the first endplate and the second endplate, and a first and second plurality of hubs that are rotatably disposed on the plurality of pins. The plurality of pins have different lengths. The plurality of adjustment arms are rotatably connected to the first and second plurality of hubs. The first plurality of hubs are axially slidable on the plurality of pins. The second plurality of hubs are axially stationary on the plurality of pins

BRIEF DESCRIPTION OF THE DRAWINGS

Accompanying this written specification is a collection of drawings of exemplary embodiments of the present disclosure. One of ordinary skill in the art would appreciate that these are merely exemplary embodiments, and additional and alternative embodiments may exist and still within the spirit of the disclosure as described herein.

FIG. 23 illustrates a perspective view of an exemplary disclosed lower endplate, with dual pivot hubs and hub pins attached;

FIG. 24 illustrates a perspective view of an exemplary disclosed height drive block;

FIG. 25 illustrates a perspective view of the exemplary disclosed height drive block sectioned;

DETAILED DESCRIPTION AND INDUSTRIAL APPLICABILITY

The exemplary disclosed system, apparatus, and method may be an expandable implant. For example, the exemplary disclosed system, apparatus, and method may be a lumbar intervertebral implant. The exemplary disclosed system, apparatus, and method may include dual independent expansion capabilities. The exemplary disclosed system, apparatus, and method may be an implant having a height that may be adjusted (e.g., expanded) and/or a lordotic angle that may be adjusted. The exemplary disclosed dual expansion capabilities may be controlled independently of each other. For example, an adjustment such as an expansion of the height and the lordotic angle may be controlled independently of one another. In at least some exemplary embodiments and as described for example herein, exemplary disclosed endplates of the exemplary disclosed apparatus may be adjusted in parallel to one another, and then the lordotic angle may be modified in order to suitably fit (e.g., best fit) a patient's anatomy.

FIGS. 1-37 illustrates an exemplary embodiment of the exemplary disclosed system, apparatus, and method. Implant 10 may be a lumbar intervertebral implant. For example, implant 10 may be a dual expanding, lumbar intervertebral implant.

Figure 1:
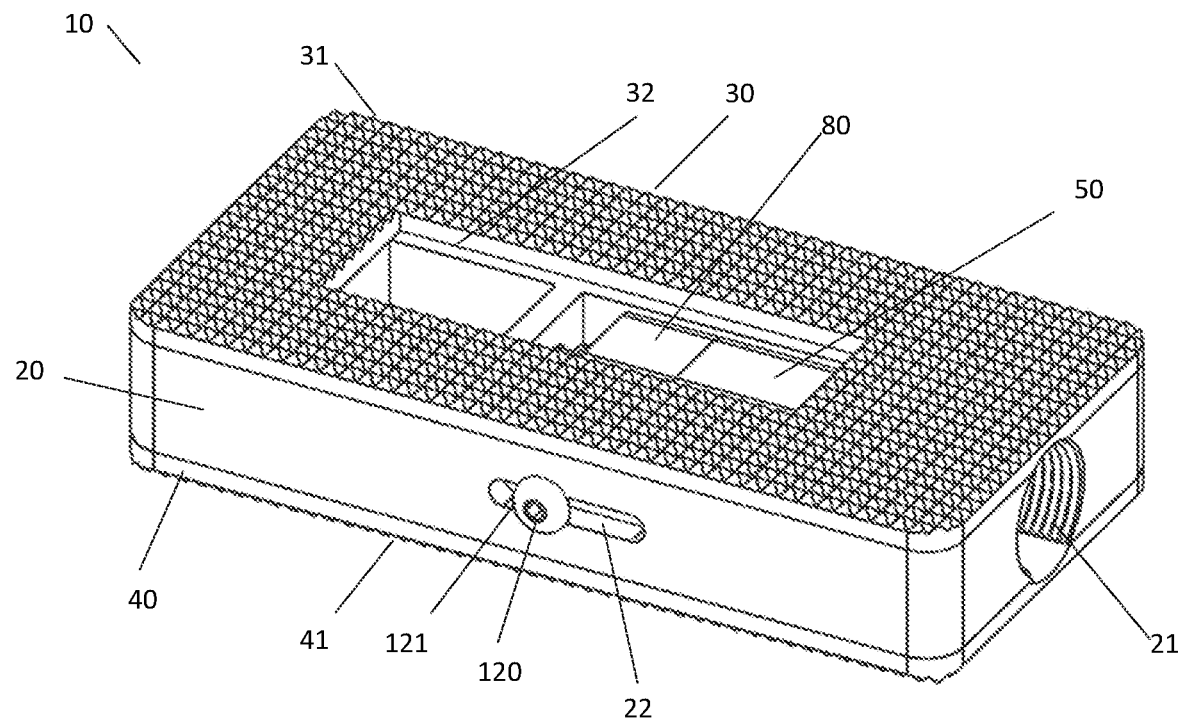
FIG. 1 illustrates a perspective view of an exemplary device in unexpanded position.
Figure 2:
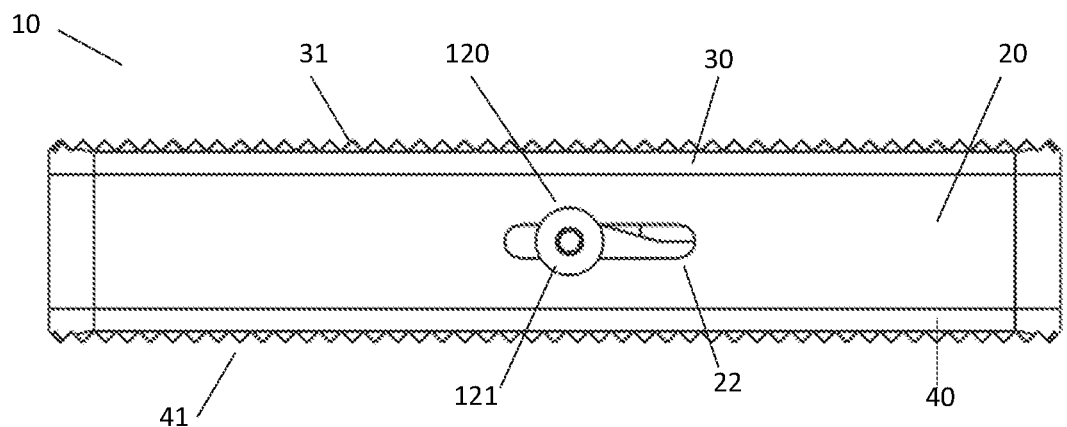
FIG. 2 illustrates an anterior view of the exemplary disclosed device in unexpanded position.
Figure 6:
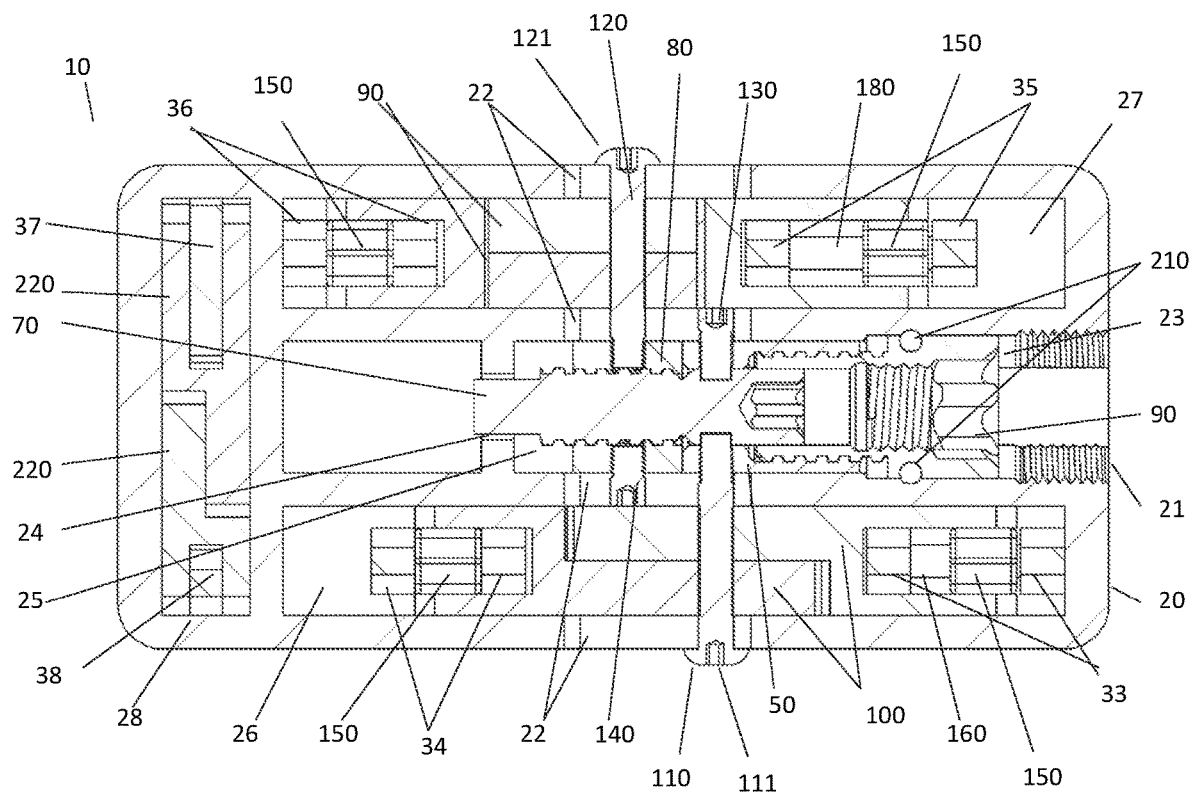
FIG. 6 illustrates a section view of the exemplary device in unexpanded position with anterior face at top, looking from the bottom up.
Figure 7:
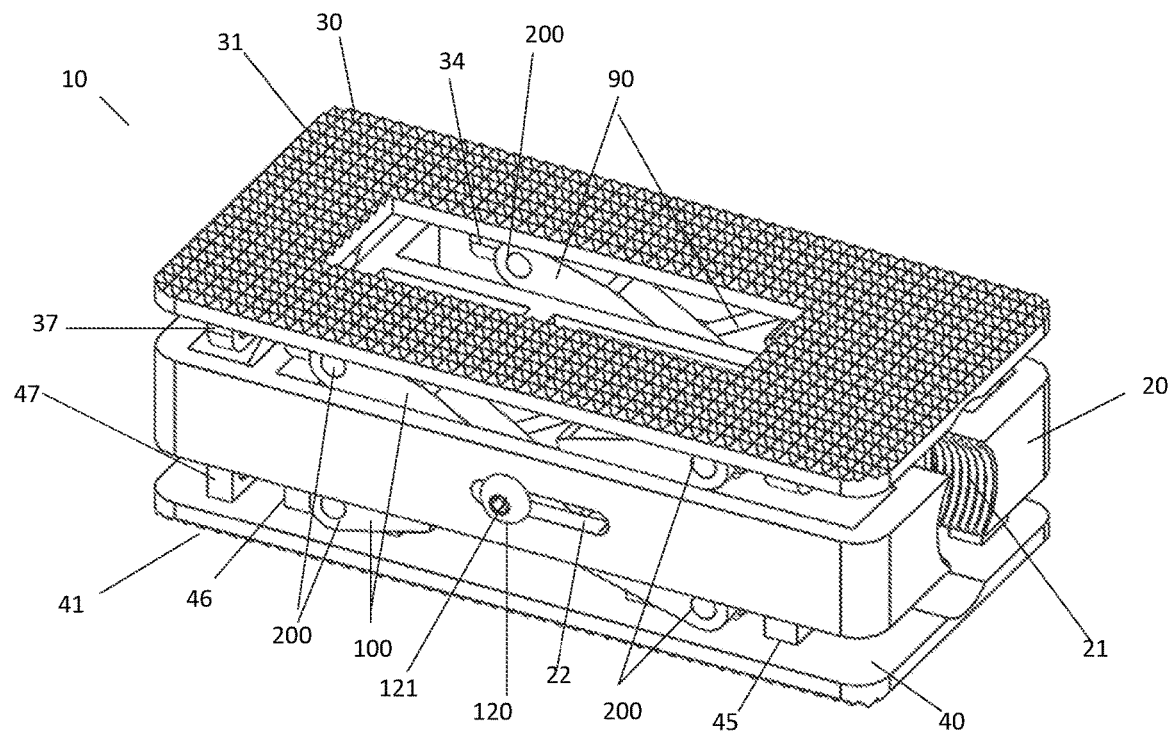
FIG. 7 illustrates a perspective view of the exemplary device in parallel expanded position.
Figure 8:
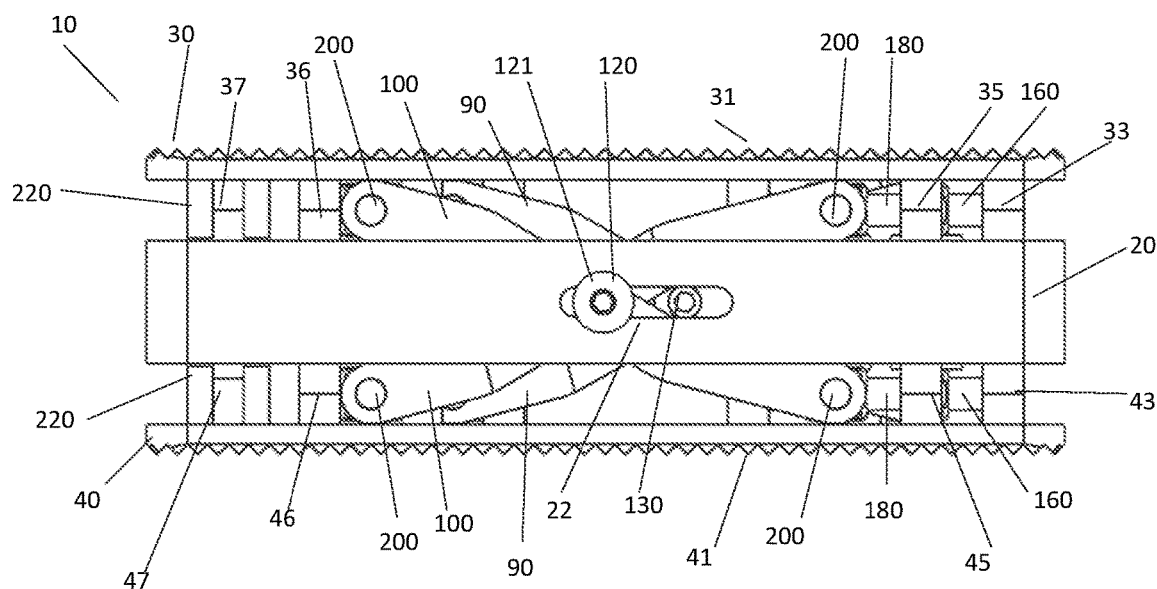
FIG. 8 illustrates an anterior view of the exemplary device in parallel expanded position.
Figure 37:
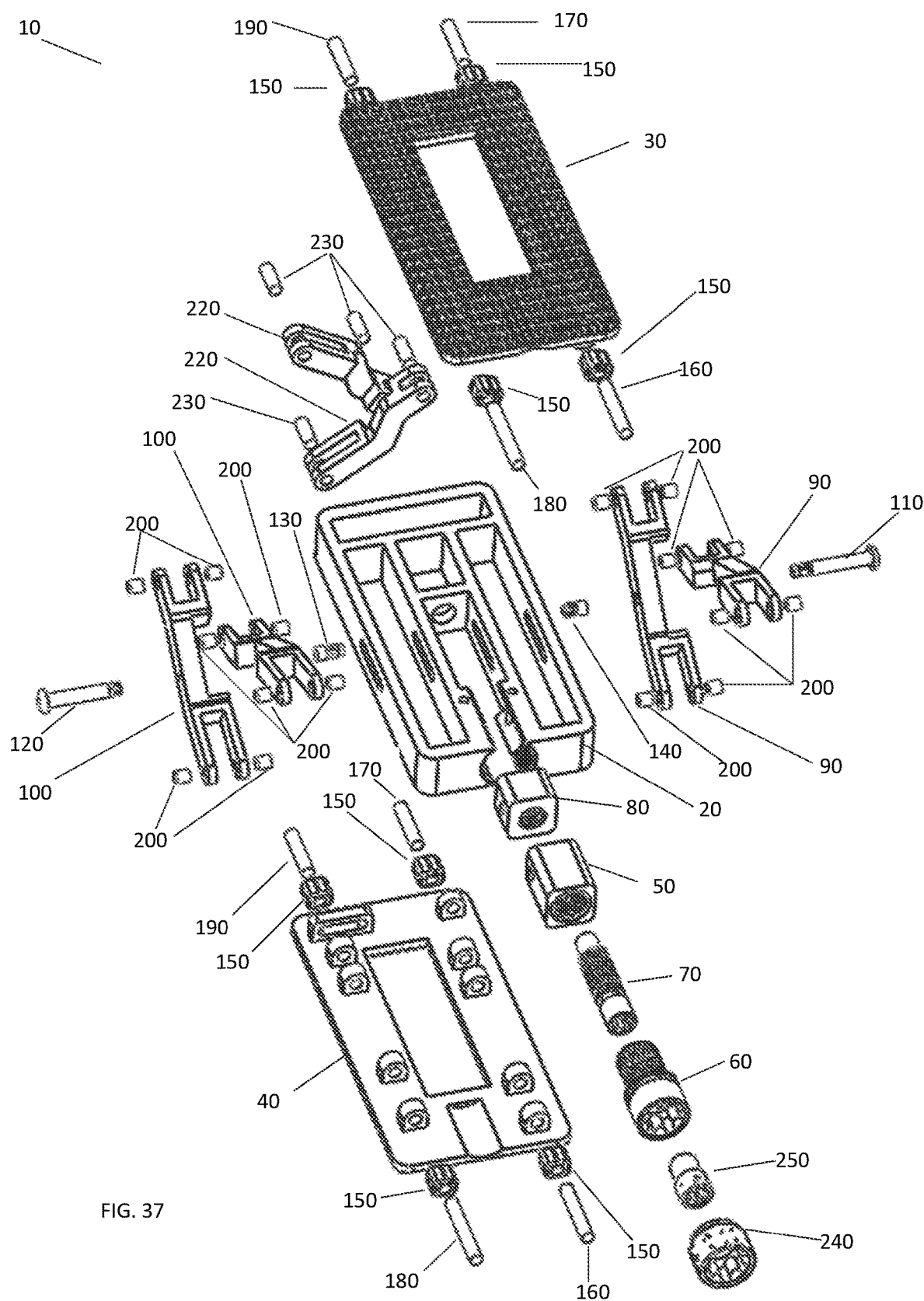
FIG. 37 illustrates an exploded view of the exemplary disclosed device.

In at least some exemplary embodiments and as illustrated in FIG. 37, implant 10 may include a base 20 with an upper endplate 30 and lower endplate 40. The upper endplate 30 and lower endplate 40 are connected to each other via a pair of height adjustment arms 90, a pair of lordosis adjustment arms 100, and a pair of cross braces 220. In turn, the pair of height adjustment arms 90 are linked to a height drive block 50 via a height adjustment pin 110. The height drive block 50 sits within a block cavity 25 of the base 20, for example as illustrated in FIG. 6. Likewise, as illustrated in FIG. 1, the pair of lordosis adjustment arms 100 are linked to a lordosis drive block 80 via a lordosis adjustment pin 120. The lordosis drive block 80 sits within the block cavity 25 of the base 20, for example as illustrated in FIG. 6. Returning to FIG. 37, the positions of the height drive block 50 and lordosis drive block 80 are determined by a height drive gear 60 and a lordosis drive gear 70.

Figure 15:
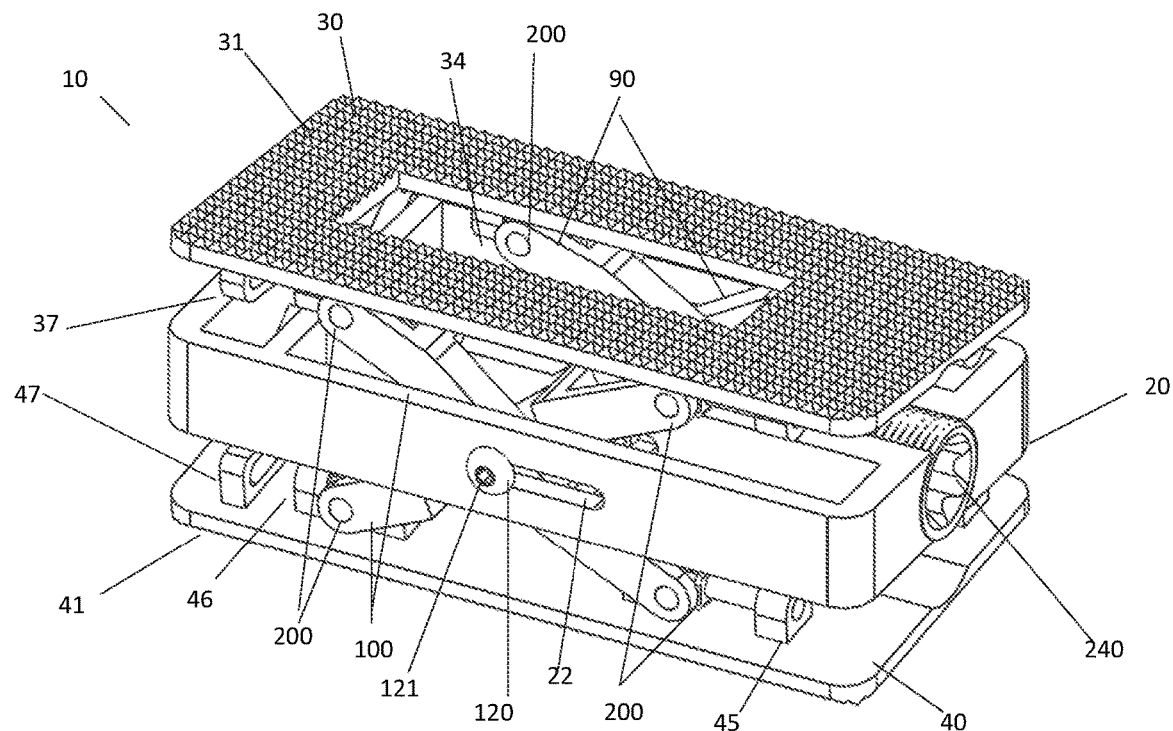
FIG. 15 illustrates a perspective view of the exemplary device in lordotic expanded position with locking screws.
Figure 16:
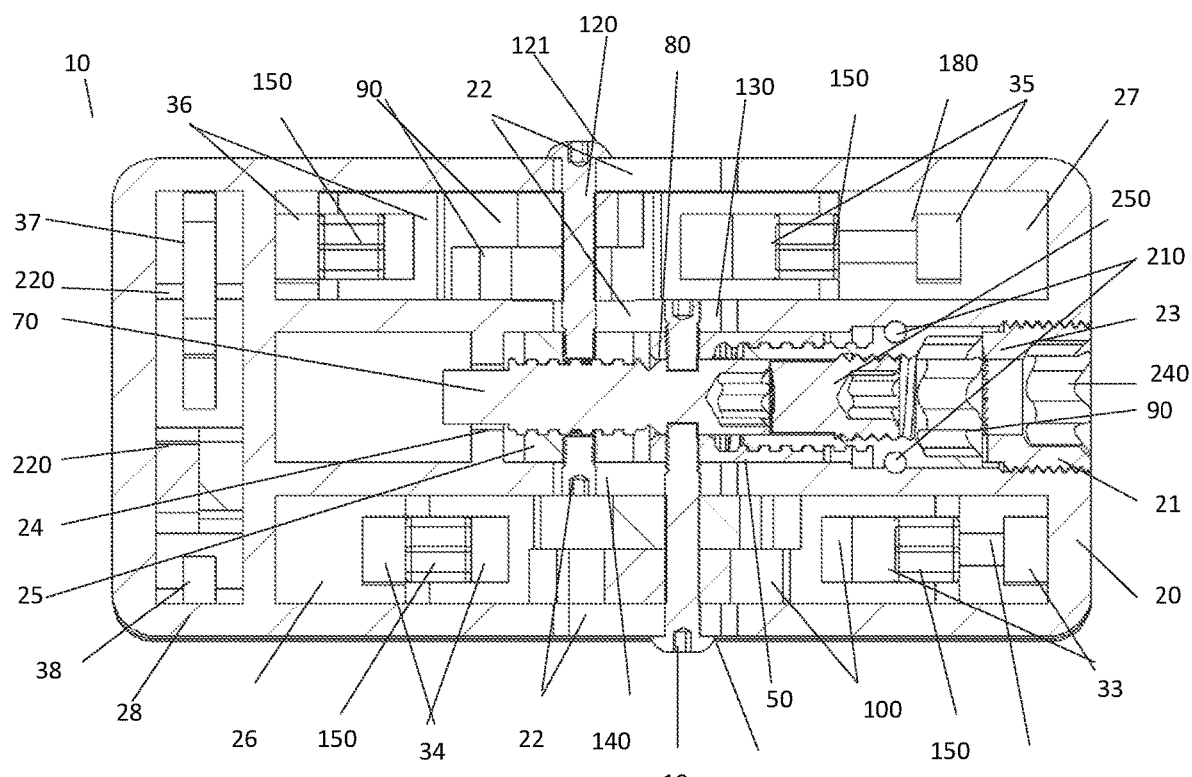
FIG. 16 illustrates a section view of the exemplary device in lordotic expanded position with anterior face at top, looking from the bottom up with lock screws.

In at least some exemplary embodiments and for example as illustrated in FIG. 1, the base component 20 is a substantially rectangular cube. Extending longitudinally from the proximal end of the base 20 is a set of inserter/locking threads 21. These threads 21 are generally left-handed or counterclockwise, and intended to mate with an inserter device (not shown for clarity) as well as a height locking screw 240 for example as illustrated in FIGS. 15 and 16. Extending from the locking threads 21 is a height gear cylindrical cavity 23, which allows the height drive gear 60 to spin freely inside the cavity 23. The height gear cylindrical cavity 23 is intersected by a pair of retaining pin holes 29. Height gear retaining pins 210 fit into the retaining pin holes 29 and the corresponding retaining groove 62 of the height drive gear 60. This holds the height drive gear 60 in place with regards to the base 20.

Figure 3:
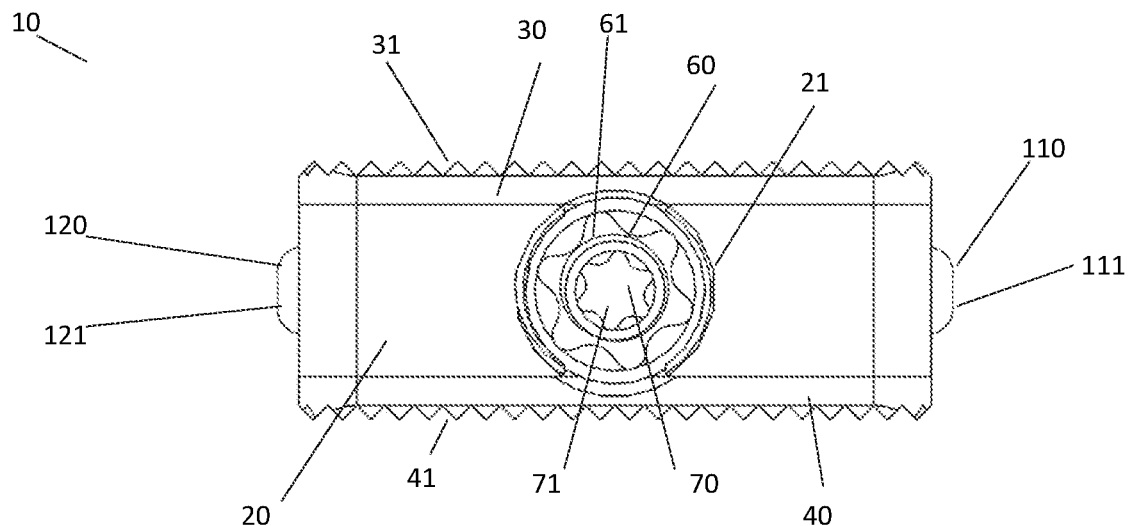
FIG. 3 illustrates a proximal view of the exemplary device in unexpanded position.
Figure 4:
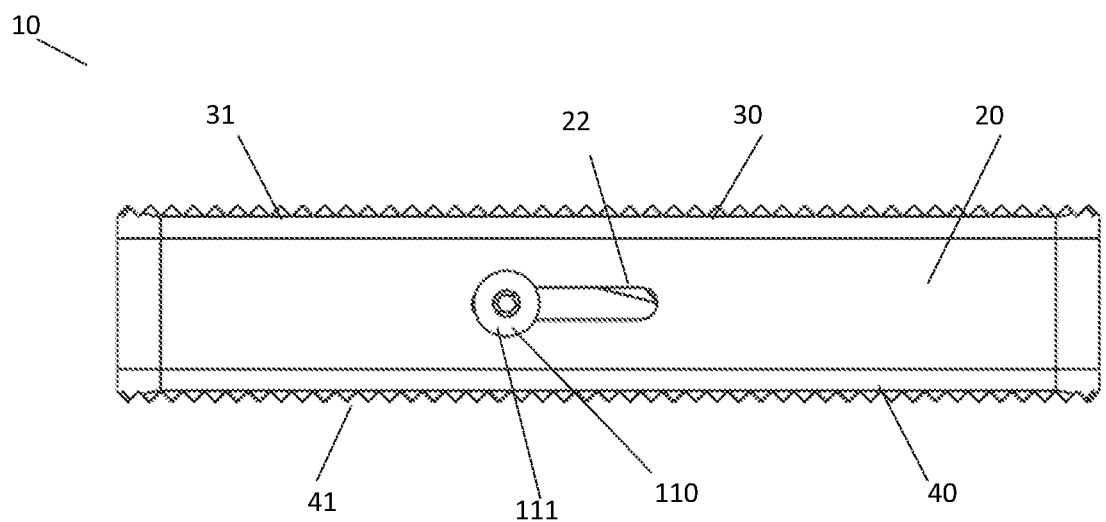
FIG. 4 illustrates a posterior view of the exemplary device in unexpanded position.
Figure 5:
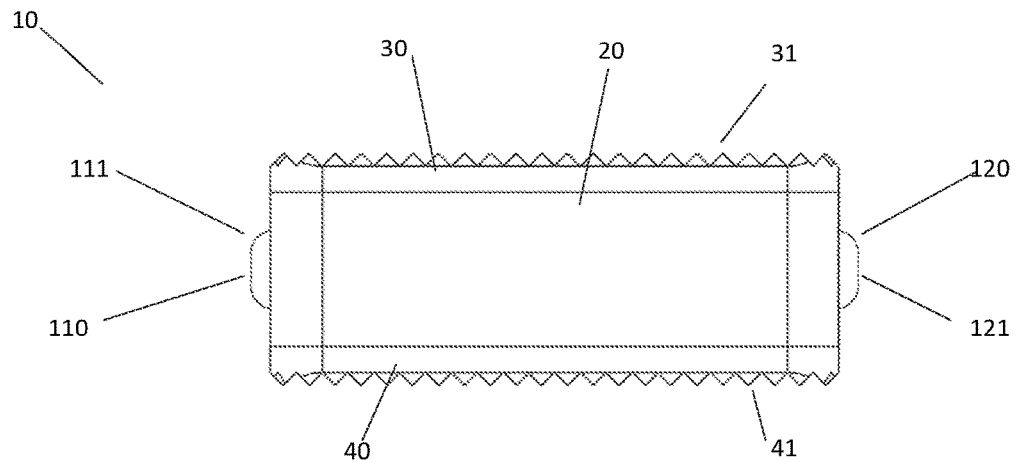
FIG. 5 illustrates a distal view of the exemplary device in unexpanded position.
Figure 9:
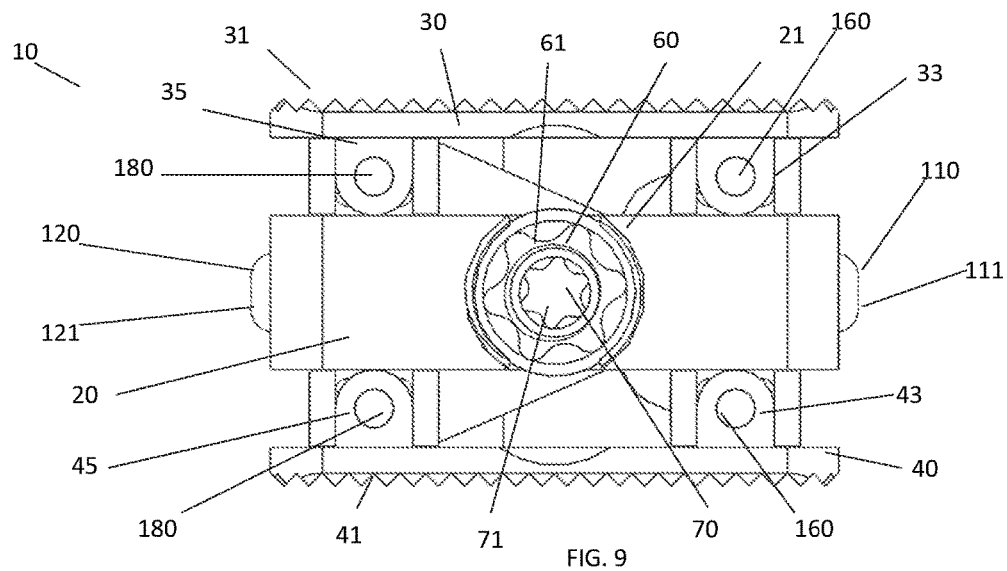
FIG. 9 illustrates a proximal view of the exemplary device in parallel expanded position.
Figure 10:
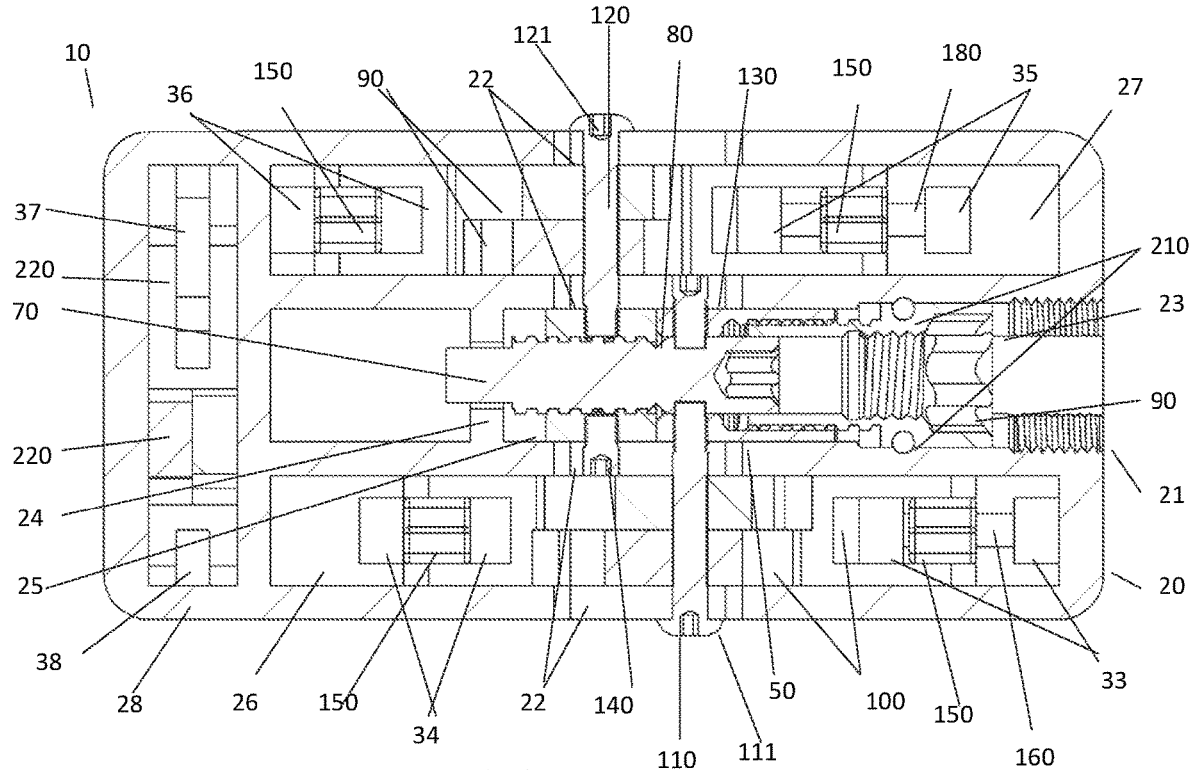
FIG. 10 illustrates a section view of the exemplary device in parallel expanded position with anterior face at top, looking from the bottom up.
Figure 11:
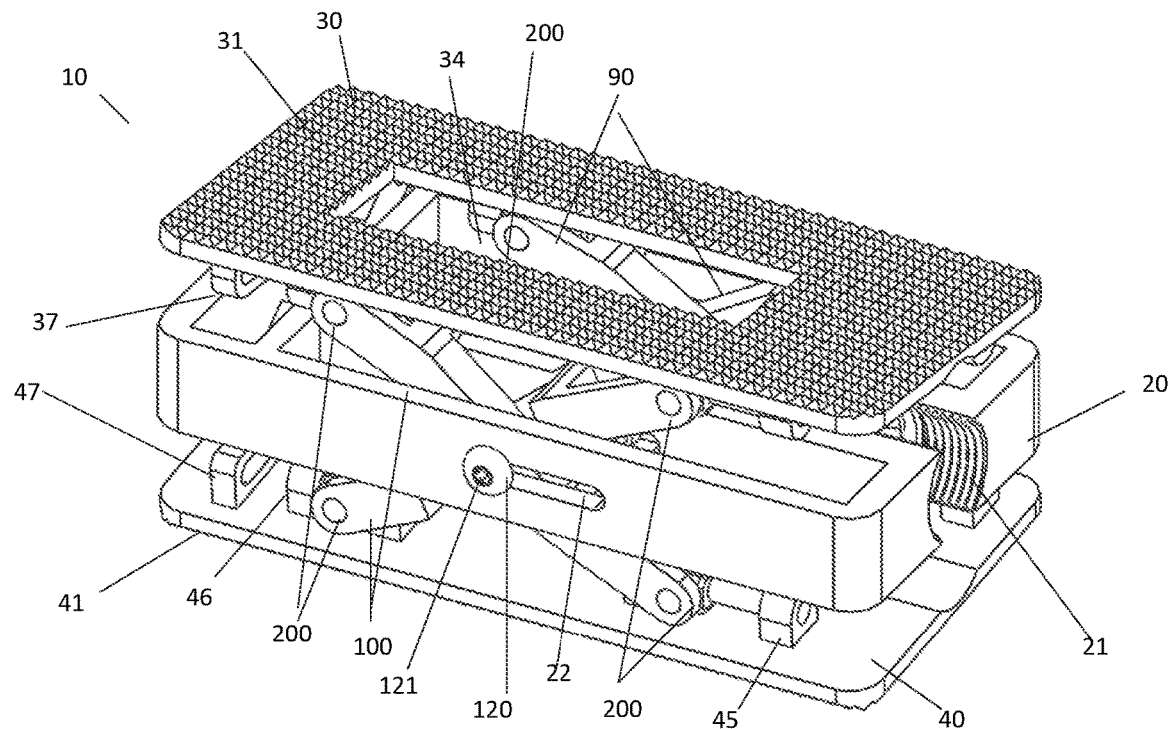
FIG. 11 illustrates a perspective view of the exemplary device in lordotic expanded position.
Figure 12:
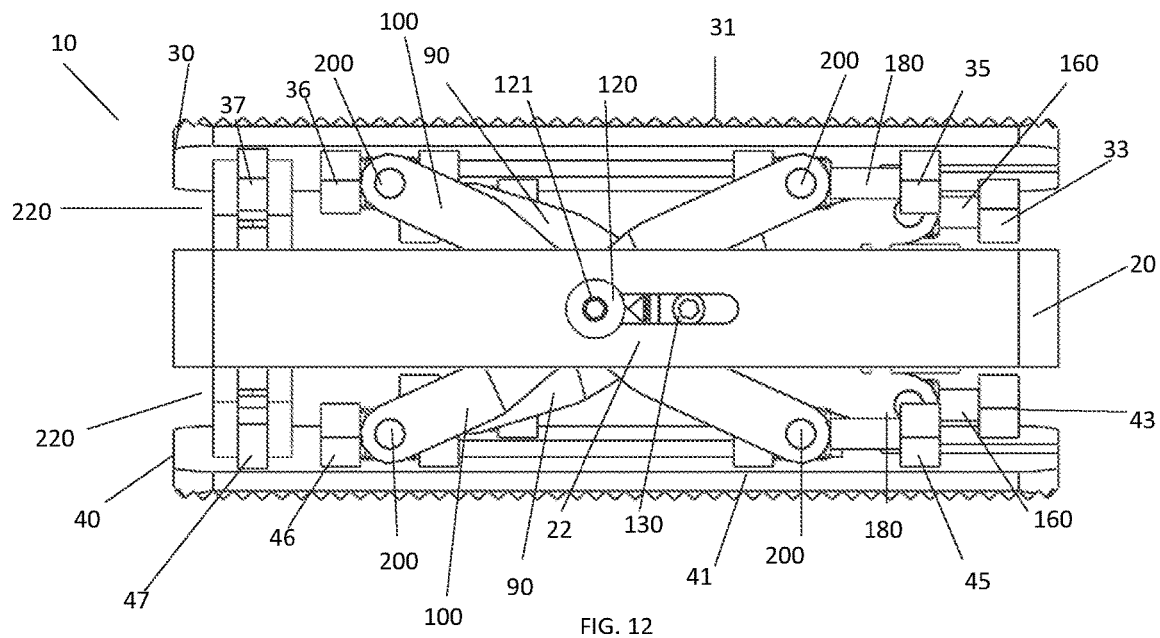
FIG. 12 illustrates an anterior view of the exemplary device in lordotic expanded position.
Figure 13:
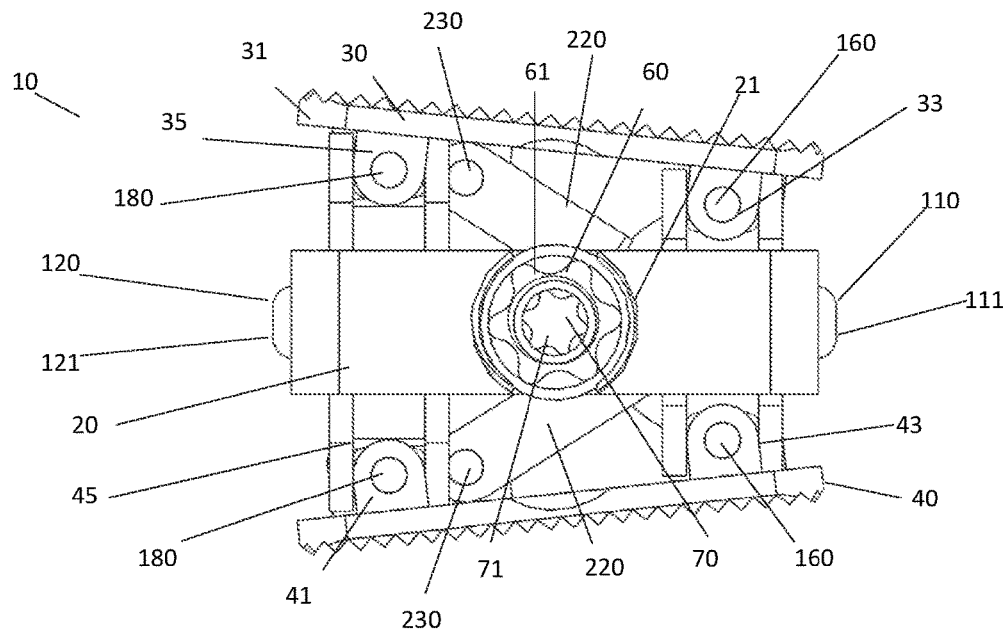
FIG. 13 illustrates a proximal view of the exemplary device in lordotic expanded position.
Figure 14:
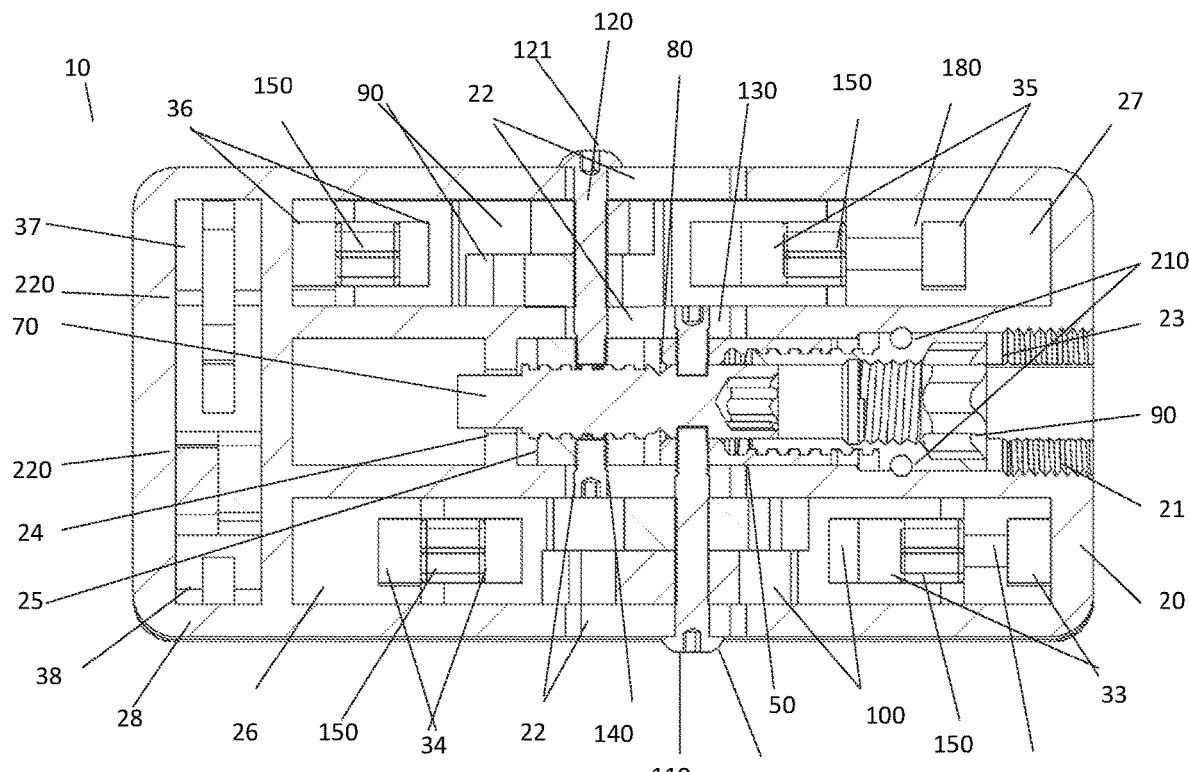
FIG. 14 illustrates a section view of the exemplary device in lordotic expanded position with anterior face at top, looking from the bottom up.
Figure 17:
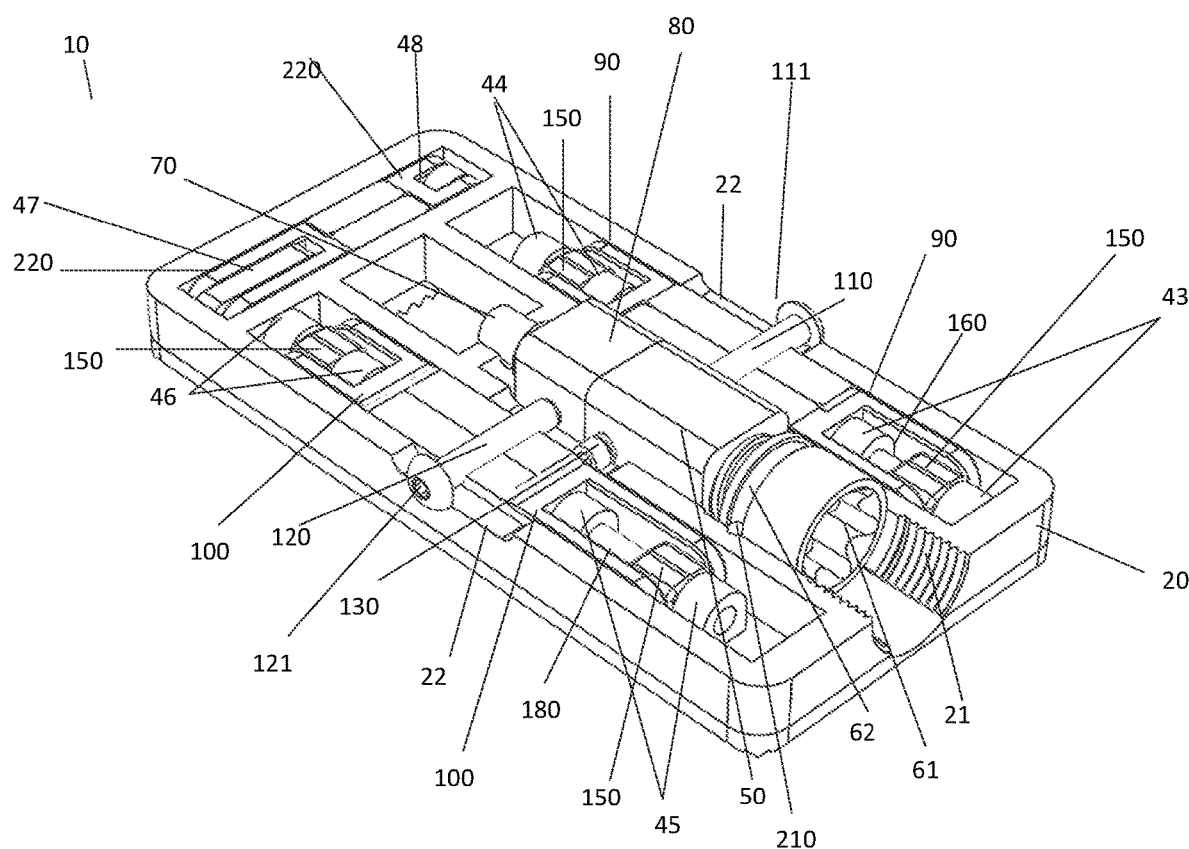
FIG. 17 illustrates a perspective view of the exemplary device in unexpanded position with body component, arms, and cross braces sectioned.
Figure 18:
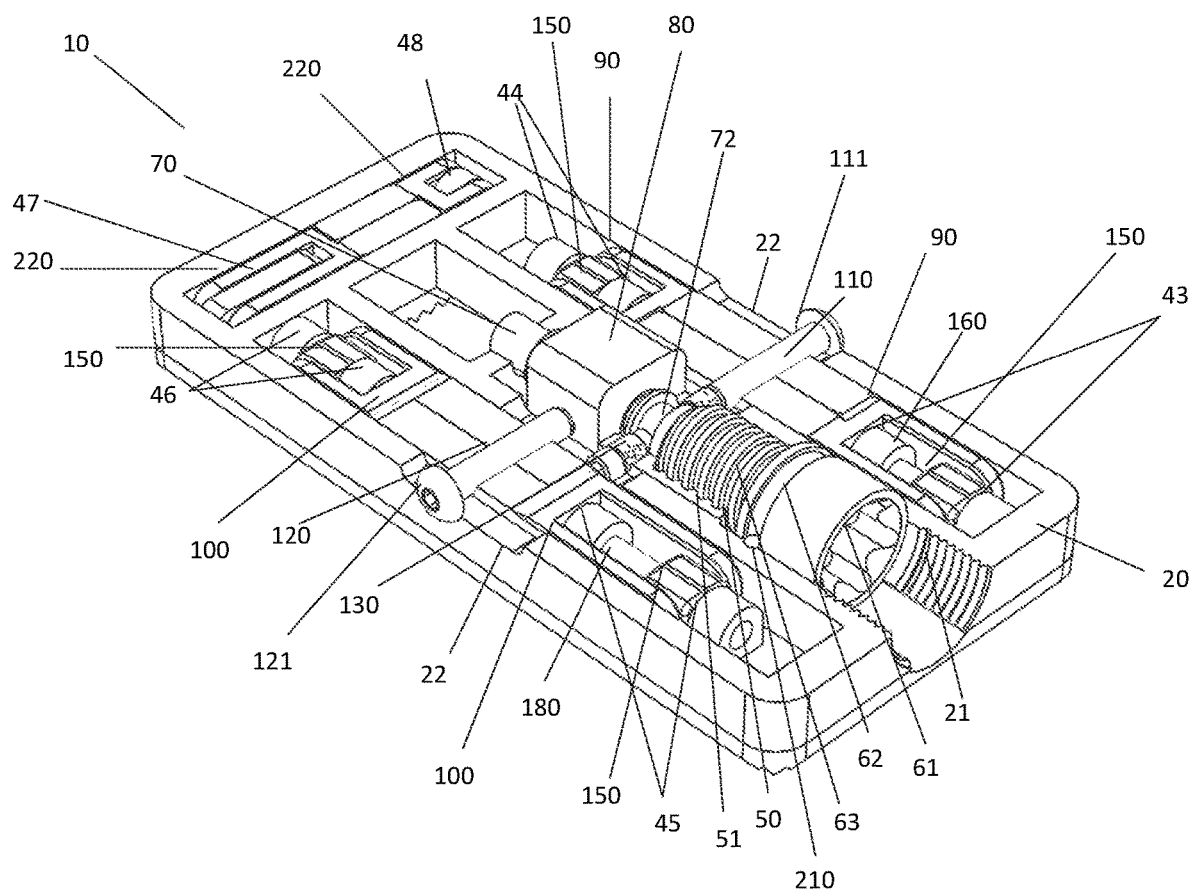
FIG. 18 illustrates a perspective view of the exemplary device in unexpanded position with body component, arms, cross braces, and height drive block sectioned.
Figure 20:
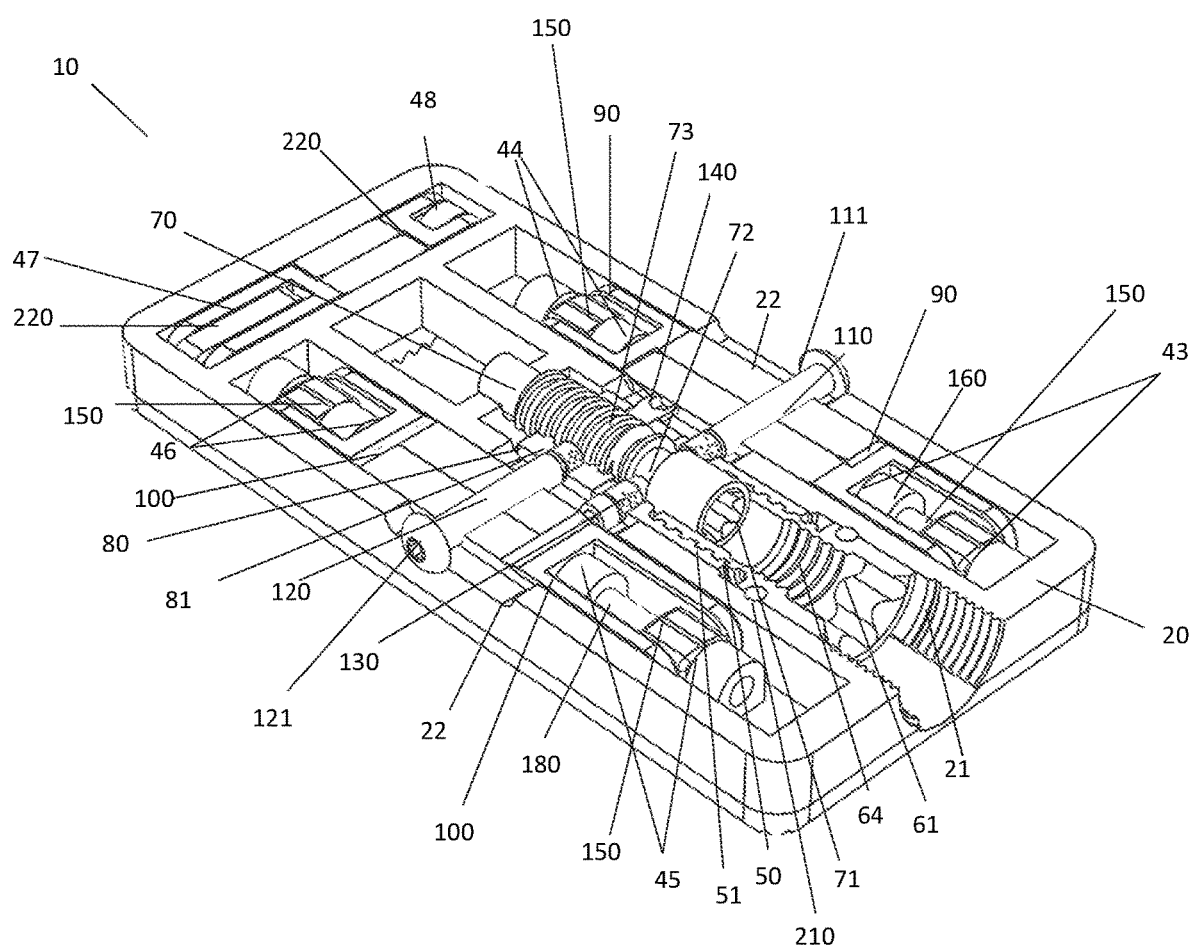
FIG. 20 illustrates a perspective view of the exemplary device in unexpanded position with body component, arms, cross braces, height drive block, lordosis drive block, and height drive gear sectioned.

In at least some exemplary embodiments, the height drive gear 60 is generally cylindrical and hollow. At the proximal end is a drive feature 61 which allows it to be rotated by a screwdriver device (not shown for clarity), for example as illustrated in FIGS. 3 and 9. Just distal of the drive feature 61 is an external retaining groove 62 which mates with the height gear retaining pins 210, for example as illustrated in FIG. 17. Distal of the retaining groove 62 is an external drive thread 63, for example as illustrated in FIG. 18. These external drive threads 63 are right-handed or clockwise threads. The external drive threads 63 mate with the internal drive threads 51 of the height adjustment block 50. Inside of the height drive gear 60 are internal locking threads 64 which are left-handed or counterclockwise threads, for example as illustrated in FIG. 20. The internal locking threads 64 mate with the lordosis locking screw 250.

In at least some exemplary embodiments, extending distally along the same axis as the height gear cylindrical cavity 23 is the rectangular block cavity 25, for example as illustrated in FIG. 6. This block cavity 25 is designed to hold the height drive block 50 and the lordosis drive block 80, allowing them to slide distally-proximally, but not rotate within the cavity 25. Running perpendicular to the block cavity 25 is a longitudinal slot 22. At the distal end of the block cavity 25, and along the same axis as the height gear cylindrical cavity 23 is a lordosis gear cylindrical cavity 24. The lordosis gear cylindrical cavity 24 holds the cylindrical tip 74 of the lordosis drive gear 70, allowing it to spin freely.

Figure 21:
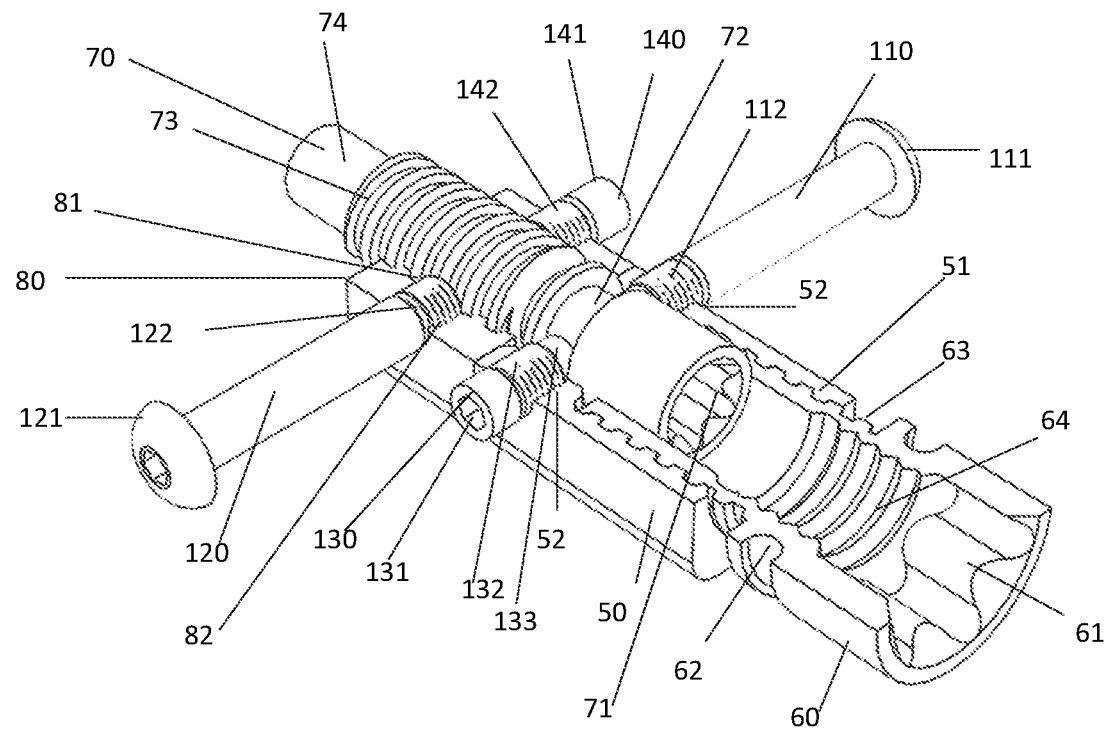
FIG. 21 illustrates a detail view of an exemplary disclosed drive assembly with height drive block, lordosis drive block, and height drive gear sectioned.
Figure 22:
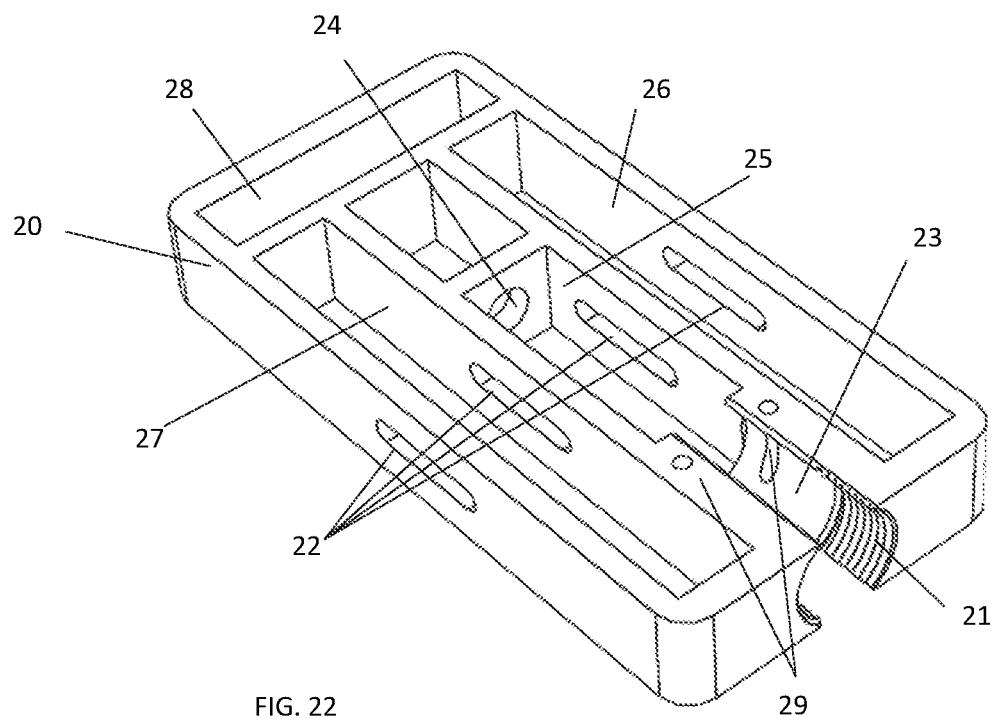
FIG. 22 illustrates a perspective view of an exemplary disclosed base component.
Figures 26, 27:
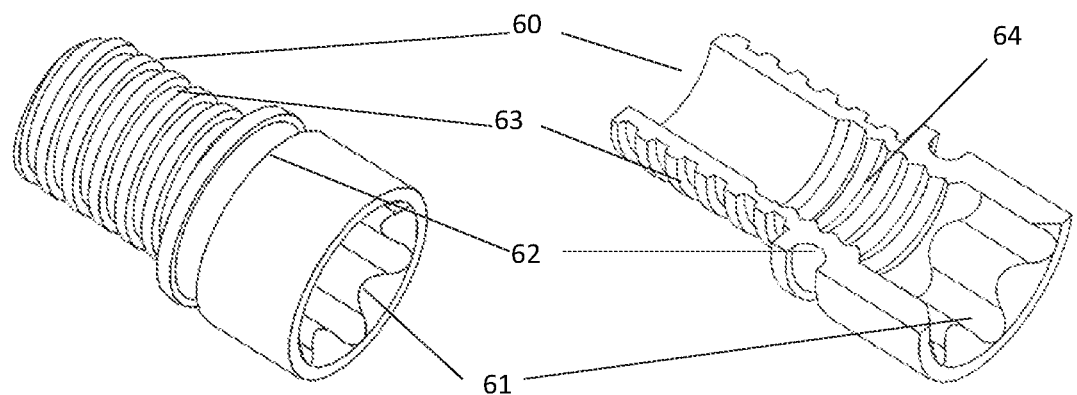
FIG. 26 illustrates a perspective view of an exemplary disclosed height drive gear.
FIG. 27 illustrates a perspective view of the exemplary disclosed height drive gear sectioned.
Figure 28:
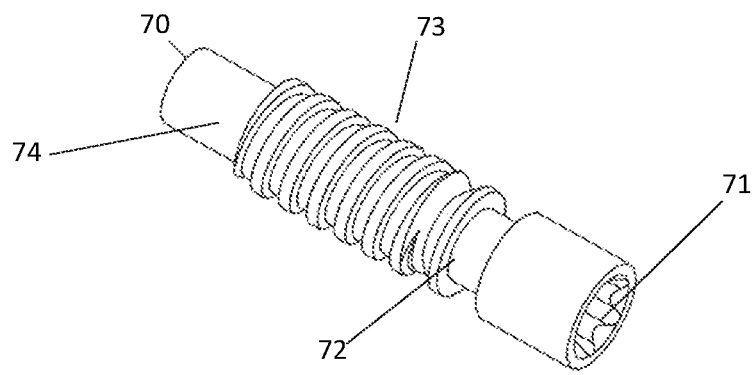
FIG. 28 illustrates a perspective view of an exemplary disclosed lordosis drive gear.
Figures 29, 30:
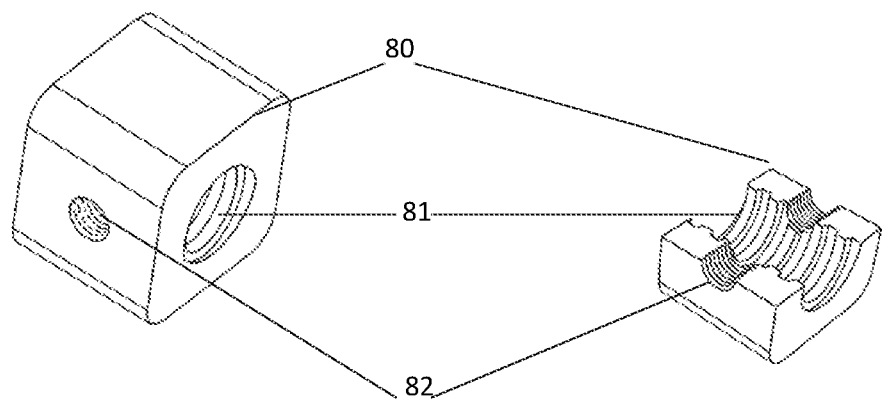
FIG. 29 illustrates a perspective view of an exemplary disclosed lordosis drive block.
FIG. 30 illustrates a perspective view of the exemplary disclosed lordosis drive block sectioned.

In at least some exemplary embodiments, the height drive block 50 threads over the height drive gear 60 using internal drive thread 51, which correspond to the external drive threads 63 of the height drive gear 60. Rotating the height drive gear 60 clockwise moves the height drive block 50 distally within the block cavity 25 of the base 20. These internal drive threads 51 extend from the proximal side partially through the center of the height drive block 50, for example as illustrated in FIG. 18. Distally, along the same axis as the internal drive threads 51, extends an internal cylindrical cavity 53. The internal cylindrical cavity 53 allows the lordosis drive gear 70 to sit inside of it, and rotate freely. Perpendicular to the internal cylindrical cavity 53 are adjustment pin threads 52, for example as illustrated in FIG. 21. The threaded portion 112 of the height adjustment pin 110 threads into the posterior adjustment pin threads 52, while the threaded portion 132 of the height adjustment counter pin 130 threads into the anterior adjustment pin threads 52.

Figure 19:
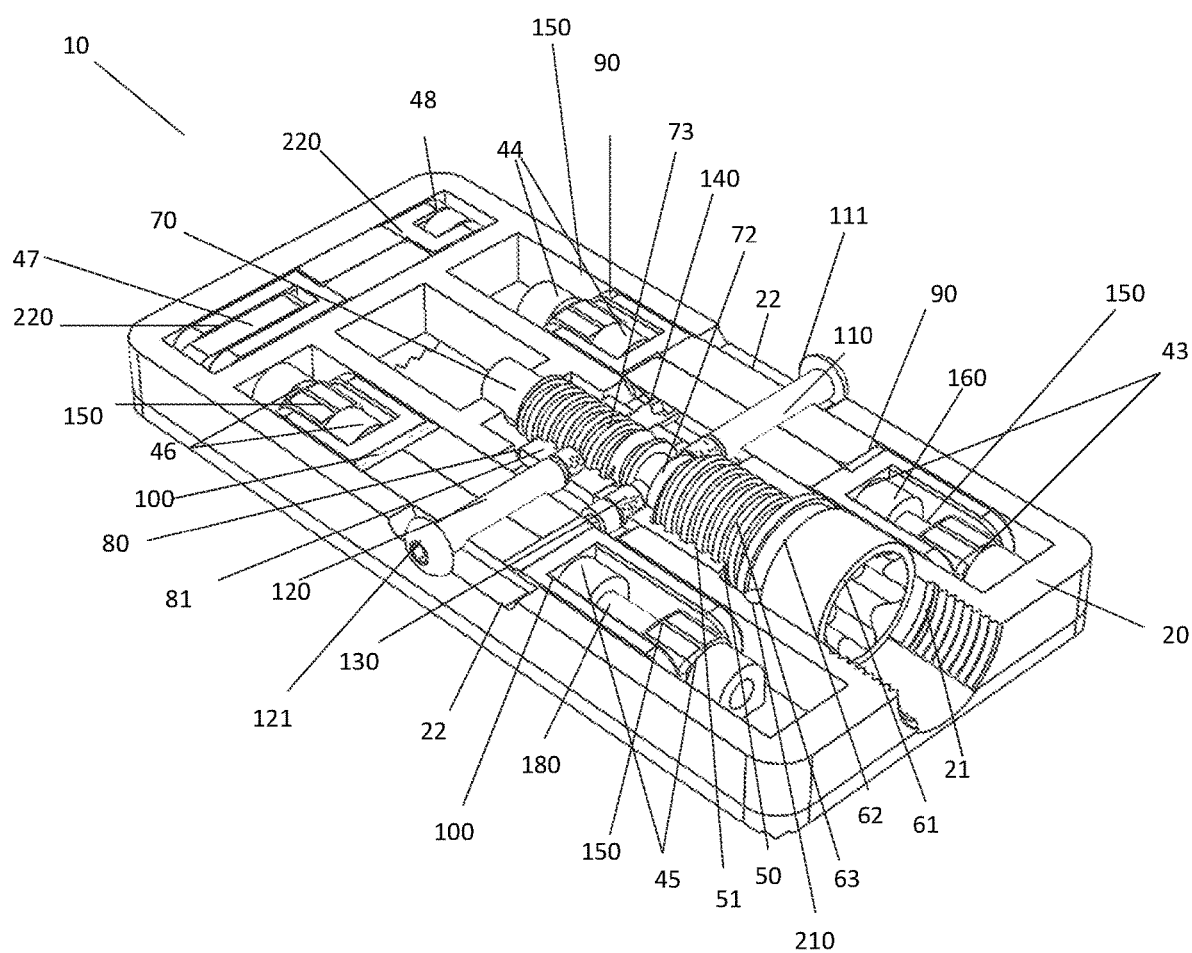
FIG. 19 illustrates a perspective view of the exemplary device in unexpanded position with body component, arms, cross braces, height drive block, and lordosis drive block sectioned.

In at least some exemplary embodiments, the lordosis drive gear 70 is generally cylindrical. The proximal portion of the lordosis drive gear 70 has an internal drive feature 71 which allows it to be rotated by a screwdriver device (not shown for clarity). Just distal of the drive feature 71 is an external retaining groove 72 which mates with the retaining tip 113 of the height adjustment pin 110 and the retaining tip 133 of the height adjustment counter pin 130. The retaining tips 113, 133 extend through the adjustment threads 52 of the height drive block 50. This captures the lordosis drive gear 70 within the height drive block 50 while allowing it to rotate. So, as the height drive block 50 moves distally within the base 20, the lordosis drive gear 70 moves with the height drive block 50. Distal of the retaining groove 72 is an external drive thread 73, for example as illustrated in FIG. 19. These external drive threads 73 are right-handed or clockwise threads. The external drive threads 73 mate with the internal drive threads 81 of the height adjustment block 80. The distal cylindrical tip 74 of the lordosis drive gear 70 sits within the lordosis gear cylindrical cavity 24.

In at least some exemplary embodiments, the lordosis drive block 80 threads over the lordosis drive gear 70 using internal drive thread 81, which correspond to the external drive threads 73 of the lordosis drive gear 70. Rotating the lordosis drive gear 70 clockwise moves the lordosis drive block 80 distally within the block cavity 25 of the base 20. These internal drive threads 81 extend from the entire lordosis drive block 80, for example as illustrated in FIG. 19. Perpendicular to the internal drive threads 81 are adjustment pin threads 82. The threaded portion 122 of the lordosis adjustment pin 120 threads into the anterior adjustment pin threads 82, while the threaded portion 142 of the lordosis adjustment counter pin 140 threads into the posterior adjustment pin threads 82. Unlike the height adjustment pin 120 and height adjustment counter pin 130, the lordosis adjustment pin 120 and lordosis adjustment counter pin 140 do not touch or interact with the lordosis drive gear 70.

In at least some exemplary embodiments, extending parallel to the block cavity 25 of the base 20 on the posterior side is the rectangular height arm cavity 26, for example as illustrated in FIG. 6. Like the block cavity 25, the longitudinal slot 22 extends perpendicular through the height arm cavity 26. The height adjustment pin 110 passes through the longitudinal slot 22 allowing it to move distally-proximally within the longitudinal slot 22. The height arm cavity 26 also holds the pair of height adjustment arms 90. Each of these height adjustment arms 90 has a central pin hole 92 through its central beam 91. The central pin hole 92 is perpendicular to the length of the height adjustment arms 90. The height adjustment pin 110 goes through this central pin hole 92. The height adjustment arms 90 can then rotate about the height adjustment pin 110. The enlarged head 111 of the height adjustment pin 110 sits outside the base 20 to help counteract binding and unsuitable rotation along a cephalad-caudal axis. Distal to the height adjustment pin 110, the lordosis adjustment counter pin 140 also protrudes into the longitudinal slot 22, although its head 141 rests within the slot 22 and does not extend into the height arm adjustment cavity 26. The lordosis adjustment counter pin 140 helps to counter the axial rotation of the lordosis drive block 80.

In at least some exemplary embodiments, extending parallel to the block cavity 25 of the base 20 on the anterior side is the rectangular lordosis arm cavity 27. Like the block cavity 25, the longitudinal slot 22 extends perpendicular through the lordosis arm cavity 27. The lordosis adjustment pin 120 passes through the longitudinal slot 22 allowing it to move distally-proximally within the longitudinal slot 22. The lordosis arm cavity 27 also holds the pair of lordosis adjustment arms 100. Each of these lordosis adjustment arms 100 has a central pin hole 102 through its central beam 101. The central pin hole 102 is perpendicular to the length of the lordosis adjustment arms 100. The lordosis adjustment pin 120 goes through this central pin hole 102. The lordosis adjustment arms 100 can then rotate about the lordosis adjustment pin 120. The enlarged head 121 of the height adjustment pin 120 sits outside the base 20 to help counteract binding and unsuitable rotation along a cephalad-caudal axis. Proximal to the lordosis adjustment pin 120, the height adjustment counter pin 130 also protrudes into the longitudinal slot, although its head 131 rests within the slot 22 and does not extend into the lordosis arm adjustment cavity 27. The height adjustment counter pin 130 helps to counter the axial rotation of the height drive block 50.

Figure 31:
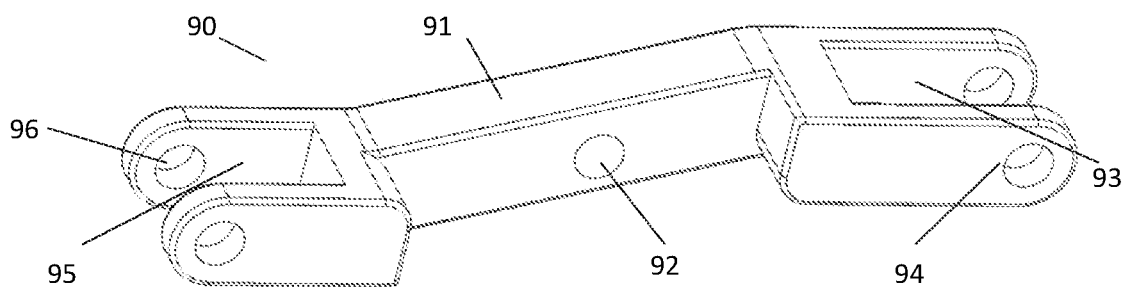
FIG. 31 illustrates a perspective view of an exemplary disclosed height adjustment arm.

In at least some exemplary embodiments, while the central pin hole 92 of the height adjustment arms 90 are constrained by the height adjustment pin 110, the proximal end is defined by an h-shaped proximal gap 93 with a proximal pin hole 94 running perpendicularly through the proximal gap 93, for example as illustrated in FIG. 31. The proximal gap 93 allows the dual pivot hub 150 to sit between its forks. Likewise, the proximal gap 93 also allows space for the proximal height hub pair 33 of the upper endplate 30 and the proximal height hub pair 43 of the lower endplate 40. The proximal gaps 93 are attached to the side holes 152 of the dual pivot hubs 150 with hub arms pins 200 through the proximal pin holes 94. The dual pivot hub 150 is in turn connected to the proximal height hub pair 33 of the upper endplate 30 via the proximal height hub pin 160 through the axial hole 151 of the dual pivot hub 150. Similarly, another dual pivot hub 150 is connected to the proximal height hub pair 43 of the lower endplate 40 via the proximal height hub pin 160 through the axial hole 151 of the dual pivot hub 150. Because the spacing of the proximal height hub pairs 33, 43 are wider than the length of the dual pivot hub 150, the dual pivot hub 150 can slide axially along the proximal height hub pin 160. Additionally, the dual pivot hub 150 can rotate around the proximal height hub pin 160.

In at least some exemplary embodiments, the distal end of the height adjustment arm 90 is defined by an h-shaped distal gap 95 with a distal pin hole 96 running perpendicularly through the distal gap 95, for example as illustrated in FIG. 31. The distal gap 95 allows the dual pivot hub 150 to sit between its forks. Likewise, the distal gap 95 also allows space for the distal height hub pair 34 of the upper endplate 30 and the distal height hub pair 44 of the lower endplate 40. The distal gaps 95 are attached to the side holes 152 of the dual pivot hubs 150 with hub arms pins 200 through the distal pin holes 96. The dual pivot hub 150 is in turn connected to the distal height hub pair 34 of the upper endplate 30 via the distal height hub pin 170 through the axial hole 151 of the dual pivot hub 150. Similarly, another dual pivot hub 150 is connected to the distal height hub pair 44 of the lower endplate 40 via the distal height hub pin 170 through the axial hole 151 of the dual pivot hub 150. Because the spacing of the distal height hub pairs 34, 44 are the same width as the length of the dual pivot hub 150, the dual pivot hub 150 cannot slide axially along the distal height hub pin 170. However, the dual pivot hub 150 can still rotate around the distal height hub pin 170.

Figure 32:
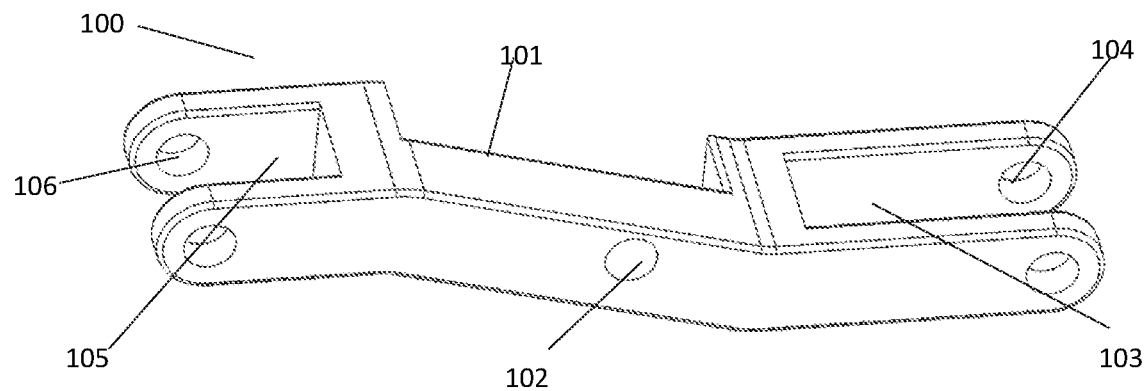
FIG. 32 illustrates a perspective view of an exemplary disclosed lordosis adjustment arm.
Figure 33:
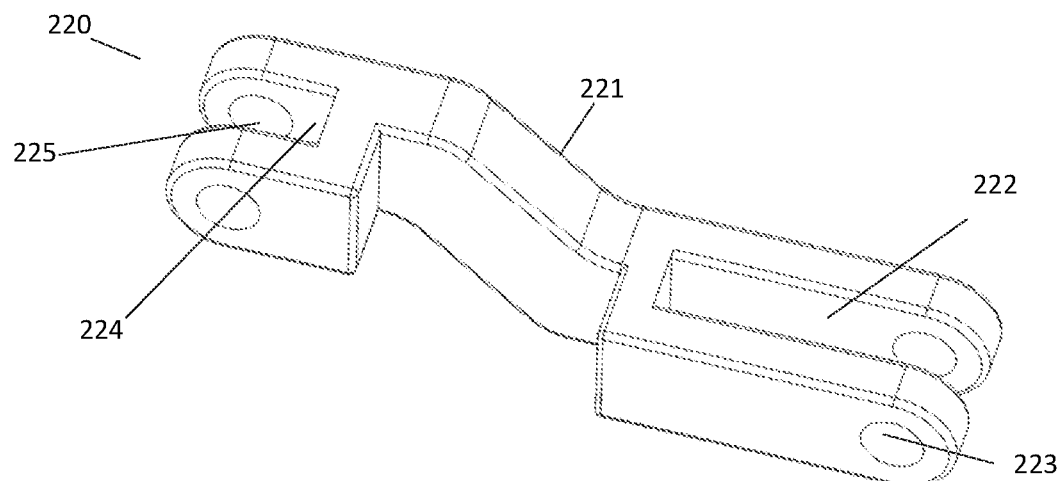
FIG. 33 illustrates a perspective view of an exemplary disclosed cross brace.
Figure 34:
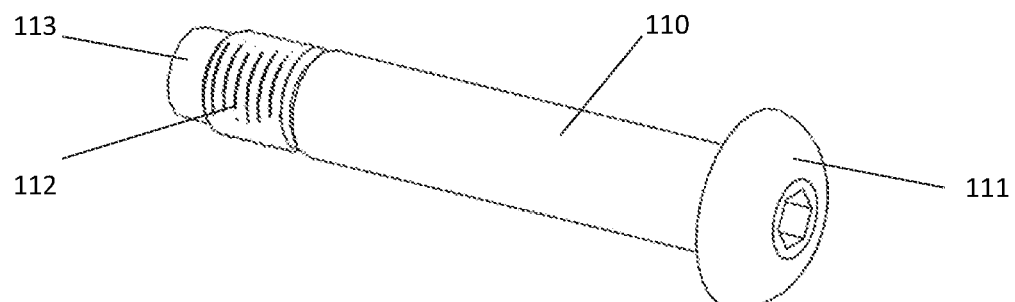
FIG. 34 illustrates a perspective view of an exemplary disclosed height adjustment pin.
Figure 35:
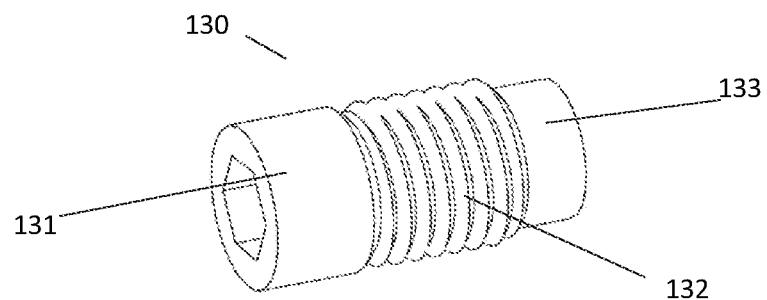
FIG. 35 illustrates a perspective view of an exemplary disclosed height adjustment counter pin.
Figure 36:
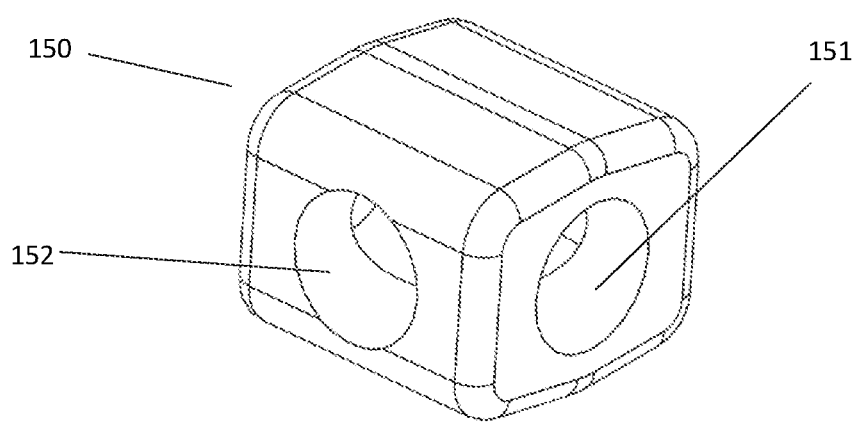
FIG. 36 illustrates a perspective view of an exemplary disclosed dual pivot block.

In at least some exemplary embodiments, while the central pin hole 102 of the lordosis adjustment arms 100 are constrained by the lordosis adjustment pin 120, the proximal end is defined by an h-shaped proximal gap 103 with a proximal pin hole 104 running perpendicularly through the proximal gap 103, for example as illustrated in FIG. 32. The proximal gap 103 allows the dual pivot hub 150 to sit between its forks. Likewise, the proximal gap 103 also allows space for the proximal lordosis hub pair 35 of the upper endplate 30 and the proximal lordosis hub pair 45 of the lower endplate 40. The proximal gaps 103 are attached to the side holes 152 of the dual pivot hubs 150 with hub arms pins 200 through the proximal pin holes 104. The dual pivot hub 150 is in turn connected to the proximal lordosis hub pair 35 of the upper endplate 30 via the proximal lordosis hub pin 180 through the axial hole 151 of the dual pivot hub 150. Similarly, another dual pivot hub 150 is connected to the proximal lordosis hub pair 45 of the lower endplate 40 via the proximal lordosis hub pin 180 through the axial hole 151 of the dual pivot hub 150. Because the spacing of the proximal lordosis hub pairs 35, 45 are wider than the length of the dual pivot hub 150, the dual pivot hub 150 can slide axially along the proximal lordosis hub pin 180. Additionally, the dual pivot hub 150 can rotate around the proximal lordosis hub pin 180.

In at least some exemplary embodiments, the distal end of the lordosis adjustment arm 100 is defined by an h-shaped distal gap 105 with a distal pin hole 106 running perpendicularly through the distal gap 105, for example as illustrated in FIG. 32. The distal gap 105 allows the dual pivot hub 150 to sit between its forks. Likewise, the distal gap 105 also allows space for the distal lordosis hub pair 36 of the upper endplate 30 and the distal lordosis hub pair 46 of the lower endplate 40. The distal gaps 105 are attached to the side holes 152 of the dual pivot hubs 150 with hub arms pins 200 through the distal pin holes 106. The dual pivot hub 150 is in turn connected to the distal lordosis hub pair 36 of the upper endplate 30 via the distal lordosis hub pin 190 through the axial hole 151 of the dual pivot hub 150. Similarly, another dual pivot hub 150 is connected to the distal lordosis hub pair 46 of the lower endplate 40 via the distal lordosis hub pin 190 through the axial hole 151 of the dual pivot hub 150. Because the spacing of the distal lordosis hub pairs 36, 46 are the same width as the length of the dual pivot hub 150, the dual pivot hub 150 cannot slide axially along the distal lordosis hub pin 190. However, the dual pivot hub 150 can still rotate around the distal lordosis hub pin 190.

In at least some exemplary embodiments, the upper endplate 30 is defined as a thin rectangular cube. On the superior face is a series of anti-migration spikes 31 intended to embed in the adjacent vertebral endplate. Extending from the interior to superior faces of the upper endplate is a graft area 32, for example as illustrated in FIG. 1. On the proximal posterior portion of the inferior face is the proximal height hub pair 33, for example as illustrated in FIG. 6. Further distally on the posterior portion of the inferior face is the distal height hub pair 34. On the proximal anterior portion of the inferior face is the proximal height hub pair 35. Further distally on the anterior portion of the inferior face is the distal height hub pair 36. Towards the posterior distal corner of the inferior face is cross brace hub 38, while in line with the cross-brace hub 38, running anterior to posterior, is the cross-brace slot hub 37.

In at least some exemplary embodiments, the lower endplate 40 is defined as a thin rectangular cube. On the inferior face is a series of anti-migration spikes 41 intended to embed in the adjacent vertebral endplate. Extending from the interior to superior faces of the upper endplate is a graft area 42, for example as illustrated in FIG. 23. On the proximal posterior portion of the superior face is the proximal height hub pair 43. Further distally on the posterior portion of the superior face is the distal height hub pair 44. On the proximal anterior portion of the superior face is the proximal height hub pair 45. Further distally on the anterior portion of the superior face is the distal height hub pair 46. Towards the posterior distal corner of the superior face is cross brace hub 48, while in line with the cross-brace hub 48, running anterior to posterior, is the cross-brace slot hub 47.

In at least some exemplary embodiments, the distal portion of the base 20 is defined by the rectangular cross-brace cavity 28, which runs perpendicular to the block cavity 25, for example as illustrated in FIG. 6. The cross-braces 220 sit inside of this cross-brace cavity 28. The cross-brace has an h-shaped posterior gap 224 with a posterior pin holes 225 running perpendicularly through the posterior gap 224. The posterior gap 224 allows the cross-brace hub 38 of the upper endplate 30 to sit between its forks. Likewise, the posterior gap 224 of the other cross-brace 220 also allows the cross-brace hub 48 of the lower endplate 40 to sit between its forks. This allows the cross-braces 220 to rotate about the cross-brace hubs 38, 48. The cross-braces 220 are connected to the cross-brace hub 38, 48 via cross-brace pins 230 through the posterior pin hole 225. The central beam 221 of the cross-brace 220 connects the posterior gap 224 to the h-shaped anterior gap 222. Like the posterior gap 224, the anterior gap 222 also has an anterior gap pin hole 223. The anterior gap 222 allows the cross-brace slot hub 37 of the upper endplate 30 to sit between its forks. Likewise, the anterior gap 222 of the other cross-brace 220 also allows the cross-braces slot hub 47 of the lower endplate 40 to sit between its forks. This allows the cross-braces 220 to slide along the cross-brace hubs 37, 47, while also rotating. The cross-braces 220 are connected to the cross-brace slot hub 37, 47 via cross-brace pins 230 through the anterior pin hole 223.

The exemplary disclosed system, apparatus, and method may be used in any suitable application involving implants for humans or animals. For example, the exemplary disclosed system, apparatus, and method may be used in any suitable application for spinal implants. In at least some exemplary embodiments, the exemplary disclosed system, apparatus, and method may be used in any suitable application for lumbar intervertebral implants.

An exemplary operation of the exemplary disclosed system will now be described. In at least some exemplary embodiments, the implant 10 is inserted between two adjacent vertebral bodies while the endplates 30,40 are in the un-expanded position, as in FIGS. 1-6. Once in place the height drive gear 60 is then rotated clockwise. This moves the height drive block 50 distally. In turn, the height drive block 50 carries the height adjustment pin 110 distally with it. The height adjustment pin 110 also pushes the central pin hole 92 of the height adjustment arms 90 distally as well. However, because the distal gap 95 and distal pin hole 96 cannot slide in relation to the distal height hub pair 34, 44 of the endplates 30, 40, it forces the endplates 30, 40 to separate away from each in a superior-inferior direction. This is aided by the cross-braces 220 which hold the endplates 30, 40 in place in the distal-proximal plane in relation to the base 20. As the endplates 30, 40 expanded, the proximal gap 93 pulls the corresponding dual pivot hub 150 along the proximal height hub pin 160.

Additionally in at least some exemplary embodiments, because the lordosis drive gear 70 is held in place in relation to height drive block 50, and because the proximal face of the lordosis drive block 80 rests against the distal face of the height drive block 50, as the height drive block 50 moves distally within the base 20, it forces the lordosis drive block 80 distally as well. Likewise, the lordosis drive block 80 carries the lordosis adjustment pin 120 distally with it. The lordosis adjustment pin 120 also pushes the central pin hole 102 of the lordosis adjustment arms 100 distally as well. However, because the distal gap 105 and distal pin hole 106 cannot slide in relation to the distal lordosis hub pair 36, 46 of the endplates 30, 40, it forces the endplates 30, 40 to separate away from each in a superior-inferior direction. This is aided by the cross-braces 220 which hold the endplates 30, 40 in place in the distal-proximal plane in relation to the base 20. As the endplates 30, 40 expand, the proximal gap 103 pulls the corresponding dual pivot hub 150 along the proximal height hub pin 180. This process creates a parallel expansion of the endplates 30, 40, because the height adjustment arms 90 and lordosis adjustment arms 100 are moving at the same time and same distance. This parallel expansion can be seen in FIGS. 7-10.

In at least some exemplary embodiments, once the desired parallel expanded height of the implant 10 is reached, the lordosis drive gear 70 can then be rotated clockwise. This moves the lordosis drive block 80 distally, while maintaining the position of the height drive block 50. Subsequently, the lordosis drive block 80 carries the lordosis adjustment pin 120 distally with it. The lordosis adjustment pin 120 also pushes the central pin hole 102 of the lordosis adjustment arms 100 distally as well. However, because the distal gap 105 and distal pin hole 106 cannot slide in relation to the distal lordosis hub pair 36, 46 of the endplates 30, 40, it forces the endplates 30, 40 to separate away from each in a superior-inferior direction. This is aided by the cross-braces 220 which hold the endplates 30, 40 in place in the distal-proximal plane in relation to the base 20. As the endplates 30, 40 expanded, the proximal gap 103 pulls the corresponding dual pivot hub 150 along the proximal height hub pin 180. Because the anterior portions of the endplates 30, 40 are expanding while the posterior portions are not, this process changes the lordotic angle of the implant 10. Additionally, because the dual pivot hubs 150 can rotate about the various hub pins 160, 170, 180, 190, the endplates 30, 40 are able to also rotate in relation to the base 20, thereby creating the lordotic angle without binding or twisting of the components. This lordotic expansion can be seen in FIGS. 11-14.

In at least some exemplary embodiments, once the desired height and lordotic angle of the implant 10 are achieved, the mechanisms can be locked into place. The height locking screw 240 is threaded into the locking threads 21 of the base 20 and up against the proximal face of the height drive gear 60. Because the height locking screw 240 is left-hand threaded and the height drive gear 60 is right-hand threaded, this prevents the height drive gear 60 from turning counterclockwise and thereby reducing the height of the implant 10. Similarly, the lordosis locking screw 250 is threaded into the locking threads 64 of the height drive gear 60 and up against the proximal face of the lordosis drive gear 70. Because the lordosis locking screw 250 is left-hand threaded and the lordosis drive gear 70 is right-hand threaded, this prevents the lordosis drive gear 70 from turning counterclockwise and thereby reducing the lordotic angle of the implant 10.

A list of exemplary parts of the exemplary disclosed system, apparatus, and method is provided below:

10—implant
20—base
  21—inserter/locking threads
  22—longitudinal slot
  23—height gear cylindrical cavity
  24—lordosis gear cylindrical cavity
  25—block cavity
  26—height arm cavity
  27—lordosis arm cavity
  28—cross brace cavity
  29—retaining pin holes
30—upper endplate
  31—anti-migration spikes
  32—graft area
  33—proximal height hub pair
  34—distal height hub pair
  35—proximal lordosis hub pair
  36—distal lordosis hub pair
  37—cross brace slot hub
  38—cross brace hub
40—lower endplate
  41—anti-migration spikes
  42—graft area
  43—proximal height hub pair
  44—distal height hub pair
  45—proximal lordosis hub pair
  46—distal lordosis hub pair
  47—cross brace slot hub
  48—cross brace hub
50—height drive block
  51—internal drive threads
  52—adjustment pin threads
  53—internal cylindrical cavity
60—height drive gear
  61—drive feature
  62—retaining groove
  63—external drive threads
  64—internal locking threads
70—lordosis drive gear
  71—drive feature
  72—retaining groove
  73—external drive threads
  74—cylindrical tip
80—lordosis drive block
  81—internal drive threads
  82—adjustment pin threads
90—height adjustment arm
  91—central beam
  92—central pin hole
  93—proximal gap
  94—proximal pin hole
  95—distal gap
  96—distal pin hole
100—lordosis adjustment arm
  101—central beam
  102—central pin hole
  103—proximal gap
  104—proximal pin hole
  105—distal gap
  106—distal pin hole
110—height adjustment pin
  111—head
  112—threaded portion
  113—retaining tip
120—lordosis adjustment pin
  121—head
  122—threaded portion
130—height adjustment counter pin
  131—head
  132—threaded portion
  133—retaining tip
140—lordosis adjustment counter pin
  141—head
  142—threaded portion
150—dual pivot hub
  151—axial hole
  152—side hole
160—proximal height hub pin
170—distal height hub pin
180—proximal lordosis hub pin
190—distal lordosis hub pin
200—hub arm pin
210—height gear retaining pin
220—cross brace 221—central beam
222—anterior gap
223—anterior pin hole
224—posterior gap
225—posterior pin hole
230—cross brace pin
240—height locking screw
250—lordosis locking screw In at least some exemplary embodiments, the exemplary disclosed implant may include a first endplate, a second endplate, a base disposed between the first endplate and the second endplate, a plurality of adjustment arms operably connecting the base with the first endplate and the second endplate, and a plurality of pins disposed on at least one of the first endplate and the second endplate. The plurality of pins (e.g., pins 160, 170, 180, and 190) may have different lengths. The plurality of adjustment arms may be rotatably connected to a plurality of hubs that are axially slidable on at least some of the plurality of pins. The plurality of pins may include a first pin (e.g., pin 170 and 190) having a first length, a second pin (e.g., pin 160) having a second length that is greater than the first length, and a third pin (e.g., pin 180) having a third length that is greater than the second length. The plurality of hubs may include a first hub that is rotatably disposed on and disposed axially stationary on the first pin, a second hub that is rotatably disposed on and axially slidable on the second pin, and a third hub that is rotatably disposed on and axially slidable on the third pin. The third hub may be axially slidable over a first distance on the third pin and the second hub may be axially slidable over a second distance on the second pin, the first distance being greater than the second distance. The exemplary disclosed implant may include a height drive gear, a lordotic drive gear, a height drive block, and a lordotic drive block that are movably disposed in the base. The height drive gear may be rotatably configured to actuate both the height drive block and the lordotic drive block, and the lordotic drive gear may be rotatably configured to actuate the lordotic drive block but not the height drive block. The height drive gear may be configured to actuate the height drive block, which may be configured to actuate a height adjustment arm of the plurality of adjustment arms, which may be attached to a first hub plurality of the plurality of hubs. The first hub plurality of the plurality of hubs may axially slide on at least some of the plurality of pins based on the actuation of the height adjustment arm. The first hub plurality of the plurality of hubs may remain axially stationary on at least some of the plurality of pins based on the actuation of the height adjustment arm, the height adjustment arm moving at least one of the first endplate and the second endplate away from the base. The lordotic drive gear may be configured, following the actuation of the height drive block by the height drive gear, to actuate a lordotic adjustment arm of the plurality of adjustment arms, which may be attached to a second hub plurality of the plurality of hubs. At least one hub of the second hub plurality of the plurality of hubs may axially slide on at least some of the plurality of hubs based on the actuation of the lordotic adjustment arm. At least one hub of the second hub plurality of the plurality of hubs may remain axially stationary on at least some of the plurality of pins based on the actuation of the lordotic adjustment arm, the lordotic adjustment arm angling at least one of the first endplate and the second endplate relative to the base.

In at least some exemplary embodiments, the exemplary disclosed implant may include a first endplate, a second endplate, a base disposed between the first endplate and the second endplate, a plurality of adjustment arms, which may include a plurality of height adjustment arms and a plurality of lordotic adjustment arms, operably connecting the base with the first endplate and the second endplate, a plurality of pins disposed on at least one of the first endplate and the second endplate, and a first and second plurality of hubs that may be rotatably disposed on the plurality of pins. The plurality of pins (e.g., pins 160, 170, 180, and 190) may have different lengths. The plurality of adjustment arms may be rotatably connected to the first and second plurality of hubs. The first plurality of hubs may be axially slidable on the plurality of pins. The second plurality of hubs may be axially stationary on the plurality of pins. The plurality of pins may include a first plurality of pins (e.g., pins 170 and 190) each having a first length, a second pin (e.g., pin 160) having a second length that is greater than the first length, and a third pin (e.g., pin 180) having a third length that is greater than the second length. The second plurality of hubs may include a first stationary plurality of hubs that may be rotatably disposed on and disposed axially stationary on the first plurality of pins. The first plurality of hubs may include a second hub that may be rotatably disposed on and axially slidable on the second pin, and a third hub that may be rotatably disposed on and axially slidable on the third pin. The third hub may be axially slidable over a first distance on the third pin and the second hub may be axially slidable over a second distance on the second pin, the first distance being greater than the second distance. The plurality of height adjustment arms may be connected to the first stationary plurality of hubs and the second hub, the plurality of height adjustment arms being configured to move at least one of the first endplate and the second endplate away from the base when the second hub axially slides on the second pin. The plurality of lordotic adjustment arms may be connected to the first stationary plurality of hubs and the third hub, the plurality of lordotic adjustment arms being configured to angle at least one of the first endplate and the second endplate relative to the base when the third hub axially slides on the third pin.

In at least some exemplary embodiments, the exemplary disclosed implant may include a first endplate, a second endplate, a base disposed between the first endplate and the second endplate, a plurality of adjustment arms operably connecting the base with the first endplate and the second endplate, a first plurality of pins disposed on the first endplate, a second plurality of pins disposed on the second endplate, and a first and second plurality of hubs that are rotatably disposed on each of the first and second plurality of pins. Each of the first and second plurality of pins may have different lengths. The plurality of adjustment arms may be rotatably connected to the first and second plurality of hubs. The first plurality of hubs may be axially slidable on the first and second plurality of pins. The second plurality of hubs may be axially stationary on the first and second plurality of pins. Each of the first and second plurality of pins may include a first length plurality of pins (e.g., pins 170 and 190) each having a first length, a second pin (e.g., pin 160) having a second length that is greater than the first length, and a third pin (e.g., pin 180) having a third length that is greater than the second length. The second plurality of hubs may include a first stationary plurality of hubs that may be rotatably disposed on and disposed axially stationary on the first length plurality of pins. The first plurality of hubs may include a second hub that may be rotatably disposed on and axially slidable on the second pin, and a third hub that may be rotatably disposed on and axially slidable on the third pin.

The exemplary disclosed system, apparatus, and method may provide an efficient and effective technique for providing an implant such as a spinal implant. The exemplary disclosed system, apparatus, and method may provide an implant having a height and a lordotic angle that may be adjusted independently of each other to provide and maintain a desired position relative to a spinal column for treating spinal conditions and diseases. The exemplary disclosed system, apparatus, and method may provide for sufficient height and lordotic angle adjustment to suitably fit a patient's anatomy.

While multiple embodiments are disclosed, still other embodiments of the present disclosure will become apparent to those skilled in the art from this detailed description. There may be aspects of this disclosure that may be practiced without the implementation of some features as they are described. It should be understood that some details have not been described in detail in order to not unnecessarily obscure the focus of the disclosure. The disclosure is capable of myriad modifications in various obvious aspects, all without departing from the spirit and scope of the present disclosure. Accordingly, the drawings and descriptions are to be regarded as illustrative rather than restrictive in nature.

What is claimed is:

1. An implant, comprising:
   a first endplate and second endplate each have an inner face, wherein the inner faces of the endplates are spaced apart by a separation distance that is expandable with respect to the inner faces of the endplates;
   a base disposed between the first endplate and the second endplate, wherein the base is formed with one or more adjustment arm cavities and the one or more adjustment arm cavities have a top side covered by the first endplate and a bottom side covered by the second endplate when the endplates are in an unexpanded position;
   a drive assembly rotatably disposed in the base between a first adjustment arm cavity of the one or more adjustment arm cavities and a second adjustment arm cavity of the one or more adjustment arm cavities; wherein the drive assembly comprises a height drive gear that causes height adjustments to the endplates and a lordotic drive gear that causes lordotic adjustments to the endplates;
   a plurality of adjustment arms each having a first end attached to the first endplate and a second end attached to the second endplate, wherein actuating the drive assembly urges at least a first of the adjustment arms to increase the separation distance between the first and second endplate attached to the first adjustment arm when the endplates are moved toward an expanded position; and
   a plurality of pins disposed on at least one of the first endplate and the second endplate; wherein the plurality of adjustment arms are rotatably connected to a plurality of hubs that are axially slidable on at least some of the plurality of pins.

2. The implant of claim 1, wherein the plurality of pins include a first pin having a first length, a second pin having a second length that is greater than the first length, and a third pin having a third length that is greater than the second length.

3. The implant of claim 2, wherein the plurality of hubs includes a first hub that is rotatably disposed on and disposed axially stationary on the first pin, a second hub that is rotatably disposed on and axially slidable on the second pin, and a third hub that is rotatably disposed on and axially slidable on the third pin.

4. The implant of claim 3, wherein the third hub is axially slidable over a first distance on the third pin and the second hub is axially slidable over a second distance on the second pin, the first distance being greater than the second distance.

5. The implant of claim 1, wherein actuating the drive assembly to make the height adjustments causes the endplates to expand in a parallel alignment, with the separation distance being even across the inner faces of the endplates.

6. The implant of claim 1, wherein actuating the drive assembly to make the lordotic adjustments causes the endplates to move into a non-parallel alignment, with the separation distance being uneven across the inner faces of the endplates.

7. The implant of claim 1, wherein a first sidewall separates the drive assembly from the first adjustment arm cavity and a second side wall separates the drive assembly from the second adjustment arm cavity.

8. The implant of claim 7, wherein the first adjustment arm cavity is aligned parallel to a first lateral side of the drive assembly and the second adjustment arm cavity is aligned parallel a second lateral side of the drive assembly.

9. The implant of claim 1, wherein the plurality of adjustment arms include a plurality of height adjustment arms and a plurality of lordotic adjustment arms.

10. The implant of claim 9, wherein the plurality of height adjustment arms are retained in the first adjustment arm cavity and the plurality of lordotic adjustment arms are retained in the second adjustment arm cavity.

11. An implant, comprising:
    a first endplate and a second endplate, wherein each of the end plates has an inner surface facing an interior portion of the implant;
    a base disposed between the first endplate and the second endplate, wherein the base comprises a first plurality of side walls that define a border of a first adjustment arm cavity and a second plurality of side walls that define a border of a second adjustment arm cavity;
    a plurality of adjustment arms, including a plurality of height adjustment arms and a plurality of lordotic adjustment arms, wherein the height adjustment arms are retained within the border of the first adjustment arm cavity and the lordotic adjustment arms are retained within the border of the second adjustment arm cavity;
    one or more hub pairs formed on the inner surface of each of the endplates;
    a pin connecting between each hub of the one or more hub pairs; and
    a pivot hub rotatably disposed on each of the pins;
    wherein each end of the height adjustment arms and the lordotic adjustment arms is rotatably connected to one of the pivot hubs.

12. The implant of claim 11, wherein each of the one or more hub pairs is formed by a pair of arches configured to receive one of the pins.

13. The implant of claim 11, wherein a first plurality of hub pairs of the one or more hub pairs is spaced to permit the pivot hub retained therebetween to slide on the pin retained by the first hub pair and a second plurality of hub pairs of the one or more hub pairs is spaced to prevent the pivot hub retained therebetween from sliding on the pin retained by the second hub pair.

14. The implant of claim 13, wherein the first plurality of hub pairs includes a first hub pair and second hub pair, the distance between hubs of the first hub pair being less than the distance between hubs of the second hub pair.

15. An implant, comprising:
a first endplate;
a second endplate;
a base disposed between the first endplate and the second endplate, wherein the first and second endplate are movable between an unexpanded position and an expanded position relative to the base;
a plurality of adjustment arms, which include a plurality of height adjustment arms and a plurality of lordotic adjustment arms, each of the adjustment arms having a first end attached to the first endplate and a second end attached to the second endplate; and
a drive assembly rotatably disposed in the base, wherein the drive assembly includes,
  a height adjustment pin extending from the drive assembly through the height adjustment arms and through a first slot formed in the base, wherein the height adjustment pin slides within the first slot as the height adjustment arms move the endplates between the unexpanded position and the expanded position,
  a height drive gear operably connected to a height drive block that receives the height adjustment pin,
  a lordotic adjustment pin extending from the drive assembly through the lordotic adjustment arms and through a second slot formed in the base, wherein the lordotic adjustment pin slides within the second slot as the lordotic adjustment arms move the endplates between the unexpanded position and the expanded position, and
  a lordotic drive gear operably connected to a lordotic drive block that receives the lordotic adjustment pin.

16. The implant of claim 15, wherein the height drive gear is rotatably configured to actuate both the height drive block and the lordotic drive block and the lordotic drive gear is configured to be actuated independent of the height drive gear and actuates the lordotic drive without actuating the height drive block.

17. The implant of claim 15, the drive assembly further including a lordotic locking screw received in the height drive gear and a height locking screw received in the base, wherein the lordotic locking screw is configured to prevent the lordotic drive gear from reversing out place and height locking screw is configured to prevent the height drive gear from reversing out place.

* * * * *